United States Patent
Ghosh et al.

(10) Patent No.: US 10,246,710 B2
(45) Date of Patent: Apr. 2, 2019

(54) DOUBLE STRAND RNA AS MOLECULAR BIOPESTICIDES FOR RNA INTERFERENCE THROUGH FEEDING IN THE HEMIPTERAN INVASIVE INSECT PEST, BROWN MARMORATED STINK BUG

(71) Applicant: The United States of America, as Represented By the Secretary of Agriculture, Washington, DC (US)

(72) Inventors: Saikat Kumar B. Ghosh, Ellicott City, MD (US); Dawn E. Gundersen-Rindal, Silver Spring, MD (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 15/657,646

(22) Filed: Jul. 24, 2017

(65) Prior Publication Data
US 2018/0023083 A1     Jan. 25, 2018

Related U.S. Application Data

(60) Provisional application No. 62/366,237, filed on Jul. 25, 2016.

(51) Int. Cl.
| | | |
|---|---|---|
| *C12N 15/113* | (2010.01) | |
| *A01N 57/16* | (2006.01) | |
| *C12N 15/82* | (2006.01) | |
| *A01N 37/46* | (2006.01) | |
| *A01N 63/02* | (2006.01) | |
| *A01N 63/04* | (2006.01) | |

(52) U.S. Cl.
CPC ............ *C12N 15/113* (2013.01); *A01N 37/46* (2013.01); *A01N 57/16* (2013.01); *A01N 63/02* (2013.01); *A01N 63/04* (2013.01); *C12N 15/8218* (2013.01); *C12N 15/8286* (2013.01); *C12N 2310/14* (2013.01); *Y02A 40/162* (2018.01)

(58) Field of Classification Search
None
See application file for complete search history.

(56) References Cited

U.S. PATENT DOCUMENTS 8,906,876 B2 * 12/2014 Raemaekers .... C07K 14/43563
514/44 A

* cited by examiner

*Primary Examiner* — J. E. Angell
(74) *Attorney, Agent, or Firm* — John D. Fado; Mark D. McNemar

(57) ABSTRACT

The present disclosure provides compositions and methods of delivering double strand ribonucleic acid (dsRNA) to control the insect pest, the brown marmorated stink bug. Several dsRNA species that target genes are disclosed herein that can be used individually or in combination. The dsRNA species can be used to induce RNA-mediated interference (RNAi) to decrease target gene expression. RNAi can be used alone, or in combination with other pest control measures to target the brown marmorated stink bug.

13 Claims, 9 Drawing Sheets
(8 of 9 Drawing Sheet(s) Filed in Color)
Specification includes a Sequence Listing.

Transport in green beans immersed in water and green food color

Magenta box with BMSB feeding assay for dsRNA

BMSB feeding on green beans

Frass
Day 2    Day 3

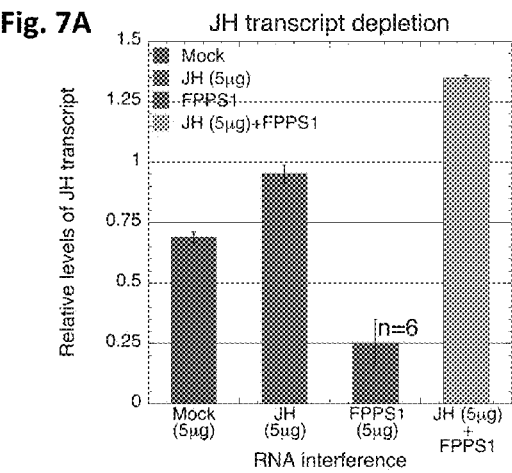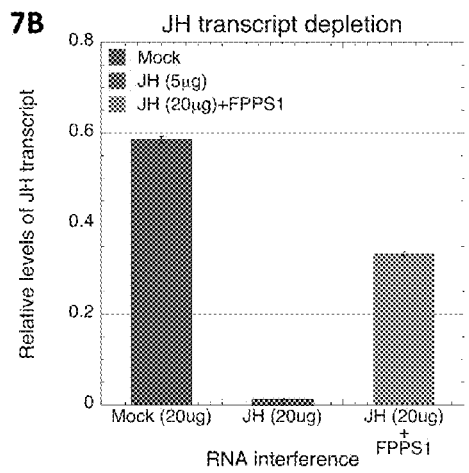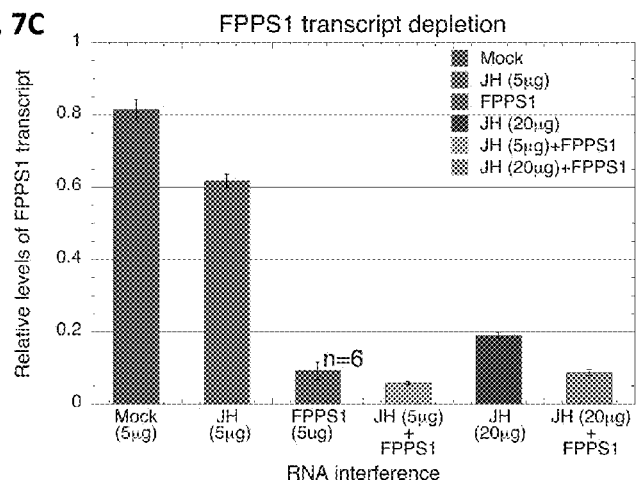

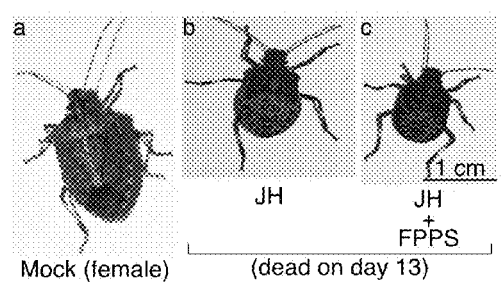
Fig. 8A
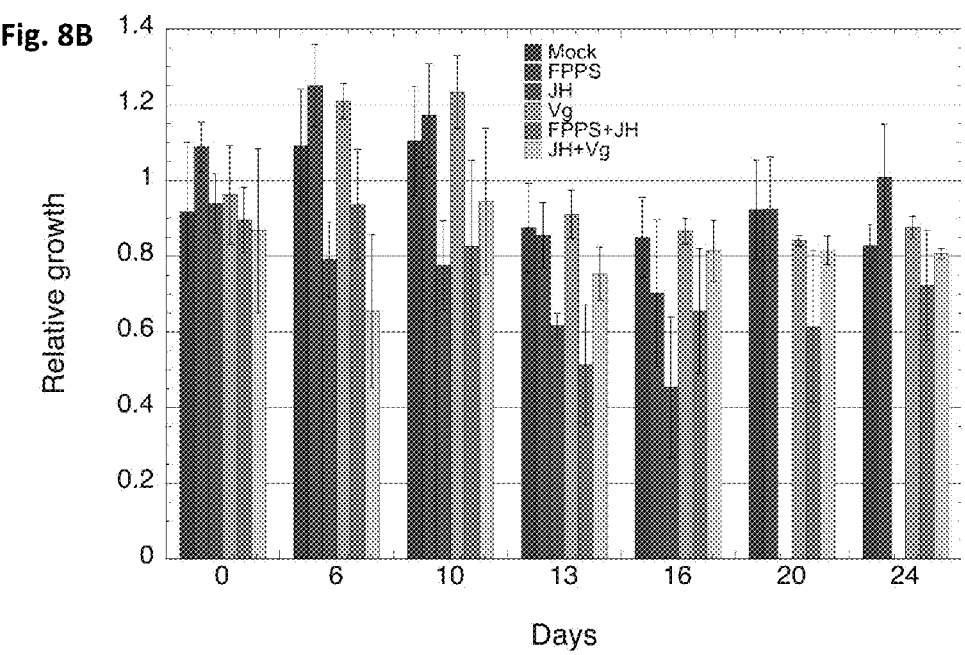

SEQUENCE LISTING

```
<160> NUMBER OF SEQ ID NOS: 94

<210> SEQ ID NO 1
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 1
caatttgatc caccgactgt t                                         21

<210> SEQ ID NO 2
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 2
ccgcatgaat cttactctgg a                                         21

<210> SEQ ID NO 3
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 3
tgcaatattg gaaataaaga agtca                                     25

<210> SEQ ID NO 4
<211> LENGTH: 21
<212> TYPE: DNA
<213> ORGANISM: Artificial Sequence
```

```
<220> FEATURE:
<223> OTHER INFORMATION: Chemically Synthesized

<400> SEQUENCE: 4
tttgtaacac catgtgccaa t                                              21

<210> SEQ ID NO 5
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 5
aaacatcatt gctcatttaa tctctt                                         26

<210> SEQ ID NO 6
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 6
aaatttggac ctgtgtaggg                                                20

<210> SEQ ID NO 7
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 7
aatgtttcgc aaggctattg                                                20

<210> SEQ ID NO 8
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 8
gtcctaaccc tgtcgtcctt                                                20

<210> SEQ ID NO 9
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 9
tcacagcaga aacaaaccaa                                                20

<210> SEQ ID NO 10
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 10
actgtgggca catatgacg                                                 19
```

```
<210> SEQ ID NO 11
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 11
cagtgcctaa cttgtttcag tg                                              22

<210> SEQ ID NO 12
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 12
ggtcttttga tgtgtttctg aag                                             23

<210> SEQ ID NO 13
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 13
atgcttgtgt gcaaggtgtt                                                 20

<210> SEQ ID NO 14
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 14
tttccctgaa ggttgttgaa a                                               21

<210> SEQ ID NO 15
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 15
tgacttcata tgcccctgtt t                                               21

<210> SEQ ID NO 16
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 16
ttgcaacaaa gaaagtgcaa a                                               21

<210> SEQ ID NO 17
<211> LENGTH: 20
<212> TYPE: DNA
<213> ORGANISM: Artificial Sequence
<220> FEATURE:
<223> OTHER INFORMATION: Chemically Synthesized
```

```
<400> SEQUENCE: 17
tgccatgaca aatgttaccc                                              20

<210> SEQ ID NO 18
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 18
tggtatcggt actttcaatc ca                                           22

<210> SEQ ID NO 19
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 19
aaaggaactt taactgccat ttg                                          23

<210> SEQ ID NO 20
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 20
tcattgcaaa tatgttgctg tat                                          23

<210> SEQ ID NO 21
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 21
atgatggcat attcggcatt                                              20

<210> SEQ ID NO 22
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 22
aatcgtcaca aggcgtacct                                              20

<210> SEQ ID NO 23
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 23
ggcaattcag ggataggaca                                              20

<210> SEQ ID NO 24
```

```
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 24
gcatcacgta ctctggcatc                                               20

<210> SEQ ID NO 25
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 25
ggatgcttat gaataatcca g                                             21

<210> SEQ ID NO 26
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 26
gtataggatt gccattttgg                                               20

<210> SEQ ID NO 27
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 27
gaattaatac gactcactat agggagacca aagttggaag ggaatga                 47

<210> SEQ ID NO 28
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 28
gaattaatac gactcactat agggagaccg catgaatctt actctgga                48

<210> SEQ ID NO 29
<211> LENGTH: 52
<212> TYPE: DNA
<213> ORGANISM: Artificial Sequence
<220> FEATURE:
<223> OTHER INFORMATION: Chemically Synthesized

<400> SEQUENCE: 29
gaattaatac gactcactat agggagatgc aatattggaa ataagaagt ca            52

<210> SEQ ID NO 30
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 30
```

```
gaattaatac gactcactat agggagattt gtaacaccat gtgccaat                    48
```

<210> SEQ ID NO 31
<211> LENGTH: 53
<212> TYPE: DNA
<213> ORGANISM: Artificial Sequence
<220> FEATURE:
<223> OTHER INFORMATION: Chemically Synthesized

<400> SEQUENCE: 31

```
gaattaatac gactcactat agggagaaaa catcattgct catttaatct ctt             53
```

<210> SEQ ID NO 32
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 32

```
gaattaatac gactcactat agggagaaaa tttggacctg tgtaggg                    47
```

<210> SEQ ID NO 33
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 33

```
gaattaatac gactcactat agggagaaat gtttcgcaag gctattg                    47
```

<210> SEQ ID NO 34
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 34

```
gaattaatac gactcactat agggagagtc ctaaccctgt cgtccctt                   47
```

<210> SEQ ID NO 35
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 35

```
gaattaatac gactcactat agggagatca cagcagaaac aaaccaa                    47
```

<210> SEQ ID NO 36
<211> LENGTH: 46
<212> TYPE: DNA
<213> ORGANISM: Artificial Sequence
<220> FEATURE:
<223> OTHER INFORMATION: Chemically Synthesized

<400> SEQUENCE: 36

```
gaattaatac gactcactat agggagaact gtgggcacat atgacg                     46
```

<210> SEQ ID NO 37
<211> LENGTH: 49
<212> TYPE: DNA

<213> ORGANISM: Artificial Sequence
<220> FEATURE:
<223> OTHER INFORMATION: Chemically Synthesized

<400> SEQUENCE: 37
gaattaatac gactcactat agggagacag tgcctaactt gtttcagtg        49

<210> SEQ ID NO 38
<211> LENGTH: 50
<212> TYPE: DNA
<213> ORGANISM: Artificial Sequence
<220> FEATURE:
<223> OTHER INFORMATION: Chemically Synthesized

<400> SEQUENCE: 38
gaattaatac gactcactat agggagaggt cttttgatgt gtttctgaag        50

<210> SEQ ID NO 39
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 39
gaattaatac gactcactat agggagaatg cttgtgtgca aggtgtt        47

<210> SEQ ID NO 40
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 40
gaattaatac gactcactat agggagattt ccctgaaggt tgttgaaa        48

<210> SEQ ID NO 41
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 41
gaattaatac gactcactat agggagatga cttcatatgc ccctgttt        48

<210> SEQ ID NO 42
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 42
gaattaatac gactcactat agggagattg caacaaagaa agtgcaaa        48

<210> SEQ ID NO 43
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 43
gaattaatac gactcactat agggagatgc catgacaaat gttaccc        47

<210> SEQ ID NO 44
<211> LENGTH: 49
<212> TYPE: DNA
<213> ORGANISM: Artificial Sequence
<220> FEATURE:
<223> OTHER INFORMATION: Chemically Synthesized

<400> SEQUENCE: 44
gaattaatac gactcactat agggagatgg tatcggtact ttcaatcca                49

<210> SEQ ID NO 45
<211> LENGTH: 50
<212> TYPE: DNA
<213> ORGANISM: Artificial Sequence
<220> FEATURE:
<223> OTHER INFORMATION: Chemically Synthesized

<400> SEQUENCE: 45
gaattaatac gactcactat agggagaaaa ggaactttaa ctgccatttg                50

<210> SEQ ID NO 46
<211> LENGTH: 50
<212> TYPE: DNA
<213> ORGANISM: Artificial Sequence
<220> FEATURE:
<223> OTHER INFORMATION: Chemically Synthesized

<400> SEQUENCE: 46
gaattaatac gactcactat agggagatca ttgcaaatat gttgctgtat                50

<210> SEQ ID NO 47
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 47
gaattaatac gactcactat agggagaatg atggcatatt cggcatt                47

<210> SEQ ID NO 48
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 48
gaattaatac gactcactat agggagaaat cgtcacaagg cgtacct                47

<210> SEQ ID NO 49
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 49
gaattaatac gactcactat agggagaggc aattcaggga taggaca                47

<210> SEQ ID NO 50
<211> LENGTH: 47
<212> TYPE: DNA
<213> ORGANISM: Artificial Sequence
<220> FEATURE:

<223> OTHER INFORMATION: Chemically Synthesized

<400> SEQUENCE: 50
gaattaatac gactcactat agggagagca tcacgtactc tggcatc　　　　　　　47

<210> SEQ ID NO 51
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 51
gaattaatac gactcactat agggagagga tgcttatgaa taatccag　　　　　　48

<210> SEQ ID NO 52
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 52
gaattaatac gactcactat agggagagta taggattgcc attttgg　　　　　　　47

<210> SEQ ID NO 53
<211> LENGTH: 45
<212> TYPE: DNA
<213> ORGANISM: Artificial Sequence
<220> FEATURE:
<223> OTHER INFORMATION: Chemically Synthesized

<400> SEQUENCE: 53
gaattaatac gactcactat agggagatga aagctggcta cagga　　　　　　　　45

<210> SEQ ID NO 54
<211> LENGTH: 45
<212> TYPE: DNA
<213> ORGANISM: Artificial Sequence
<220> FEATURE:
<223> OTHER INFORMATION: Chemically Synthesized

<400> SEQUENCE: 54
gaattaatac gactcactat agggagagca ggcttctgct tcaat　　　　　　　　45

<210> SEQ ID NO 55
<211> LENGTH: 595
<212> TYPE: DNA
<213> ORGANISM: Escherichia coli

<400> SEQUENCE: 55
tgaaagctgg ctacaggaag gccagacgcg aattattttt gatggcgtta actcggcgtt　　60 tcatctgtgg tgcaacgggc gctgggtcgg ttacggccag acagtcgtt tgccgtctga　　120 atttgacctg agcgcatttt tacgcgccgg agaaaaccgc ctcgcggtga tggtgctgcg　　180 ctggagtgac ggcagttatc tggaagatca ggatatgtgg cggatgagcg gcattttccg　　240 tgacgtctcg ttgctgcata aaccgactac acaaatcagc gatttccatg ttgccactcg　　300 ctttaatgat gatttcagcc gcgctgtact ggaggctgaa gttcagatgt gcggcgagtt　　360 gcgtgactac ctacgggtaa cagtttcttt atggcagggt gaaacgcagg tcgccagcgg　　420 caccgcgcct tcggcggtg aaattatcga tgagcgtggt ggttatgccg atcgcgtcac　　480 actacgtctg aacgtcgaaa acccgaaact gtggagcgcc gaaatcccga atctctatcg　　540

```
tgcggtggtt gaactgcaca ccgccgacgg cacgctgatt gaagcagaag cctgc        595
```

```
<210> SEQ ID NO 56
<211> LENGTH: 491
<212> TYPE: DNA
<213> ORGANISM: Halyomorpha halys

<400> SEQUENCE: 56
gttaaactag gtggctgaca agaaaaagac tcgcgactag ttcattctta agctagacac    60
cgcggagtaa gtaaactcca acacctcctt ctataagaag cgatctcgac taactacttg   120
agagtgatct cctacttctc gaactcctgc ttcttcgagg aacagattaa cccaatatgg   180
acaaaaggag tctgcttgat gatctcgatc aactaagcga acttgacgac aacccaactc   240
cccctccaca acgactagaa caaaaagaga agtatgaaac taaggtaaat aaaagaagtg   300
atgacctcct tctcgaactc ctgcttctac ttcttctgct acttcaactt agtcttggaa   360
gcgatgatag tggtaaaaca cctataggta taagtataag catcgggttt aataatttgc   420
ggaatcctga taaatacgag tccagacttg gaaacacccc gtgatggtat aggtctcatt   480
ctaagtacgc c                                                        491
```

```
<210> SEQ ID NO 57
<211> LENGTH: 374
<212> TYPE: DNA
<213> ORGANISM: Halyomorpha halys

<400> SEQUENCE: 57
acgttataac ctttatttct tcagtgttat ttagtgatta tattgtttaa taatgttatc    60
tgtaacacaa tatgtgttaa tccattgtac cgtatttgat ttaccatcga tattgtaaca   120
tagtaattta aatatgttat acatacattc gttgttattc aactaaaccg attggcttta   180
cttgtaagtc gatgtctcag tagtgtggta aagagttgcg gaaaatatat taatatctaa   240
aggatattaa attttatgga cgaaagtgaa gtctcgtcta taacttggga tagctagata   300
attcagtaat tgtaaggtaa gaaaagaac accgtttaaa tgtcaaaatg taataaccgt   360
gtaccacaat gttt                                                     374
```

```
<210> SEQ ID NO 58
<211> LENGTH: 348
<212> TYPE: DNA
<213> ORGANISM: Halyomorpha halys

<400> SEQUENCE: 58
aaacatcatt gctcatttaa tctcttaaag attctcttac atatcgattg ttttattgac    60
aaatttaaa aagaaaacaa aaagatggta ggaataattt tctatgttgt ttgtattttt   120
atgactgtta gaaatgatgt taaaaattat tgtaataaat tcatgttctg tcatcagtat   180
cttttattt tttcatttat gtttatgaat ataactatcc attctttgaa actcagaaat   240
cgtaattgta aatgaacgta ttacttatca tgtatactag tatttggtct cttcatttat   300
tagtttactg aactttgttt aaatgtaacc ctacacaggt ccaaatttt               348
```

```
<210> SEQ ID NO 59
<211> LENGTH: 404
<212> TYPE: DNA
<213> ORGANISM: Halyomorpha halys

<400> SEQUENCE: 59
```

```
ttacaaagcg ttccgataac aataataaca gtggacttat ggacattgac aaagaaaatc    60
tttcgaaatg taaatttgtt ataatattta aaattttat cttttttggg tatcctttct    120
tttggaattc ggttagagaa ctaaaccagt gacaattagt tctaccactc ttttgtaacg    180
ggatgttaac tacggatcat cgatatacaa cgttttataa ttcattgttt ttaaataaac    240 tcgttttga ccaaggttca agggcaatag aataagtgag tagtggtatg gtctccaatc     300
ttgttagtta ttttgtaagt agttcgacgc agagtcagga aagtagggtg ttttactaaa    360
attattttga tgaaatctga cttttcctg ctgtcccaat cctg                      404
```

<210> SEQ ID NO 60
<211> LENGTH: 506
<212> TYPE: DNA
<213> ORGANISM: Halyomorpha halys

<400> SEQUENCE: 60

```
agtgtcgtct ttgtttggtt gtgttgtaac aaagtcgtca tacagttatc attctccagt    60
atgactctct atattataca atactctcac atttgttaaa gaaactataa tgtcttacaa    120
taagatctca agattcgtac cgtatttttc tattaaatat attaaatttt ttcttttttt    180 acattttag ttcgttaaag agatcctctg tggttatgaa attaatcggt tggtcattta     240
gaaaggattt aaattttaga agtacgagat ccagtctcca aaagttatga cacggacgac    300
cgtgttaata agggtggatt ttttgaaaa tggttgatag tggttccttt gaatatacat     360
aagtctccac gattttact gttatcatag ctaaaactct accgaacgag cacatagcta     420
aataaaatta taaagtctaa aaattatata atcccgtttc caggggagt tgtgaaaccc     480 tcggactgca gtatacacgg gtgtca                                          506
```

<210> SEQ ID NO 61
<211> LENGTH: 524
<212> TYPE: DNA
<213> ORGANISM: Halyomorpha halys

<400> SEQUENCE: 61

```
gtcacggatt gaacaaagtc actattggta cctttgaata caaatccct gacatctttt     60 atttttacga tggttaaaat tctagcggat aactaactaa aagtttataa cctaaagact    120 ataaatctc agggatttat acaaaaggtt ctatatcttt tactttatg agaactaaaa      180 ttctagttaa cgagtacata tctaaaaaat ttttgaaaa acataaaaat tgcataattc     240
ctggaaatta taaacaact tcccatactt ttcacttta gtttgctaa acttctagct       300 tacaagtgca tagataaata aaattgaaaa acctaaaaat tgtataattt taataaacta    360
ttcaaggttt tctaattatt aattttaag gtagctaaaa ttctagaaaa ctaagttaaa     420
tatgtcataa aaagcaatga tgtggaagtt tttgtttagt tattctttag acgtttcagt    480
tttatttagt tatgtgactt agaagtcttt gtgtagtttt ctgg                      524
```

<210> SEQ ID NO 62
<211> LENGTH: 468
<212> TYPE: DNA
<213> ORGANISM: Halyomorpha halys

<400> SEQUENCE: 62

```
tacgaacaca cgttccacaa taccttaaat tctcgtcatt caaaaaagac cggtccttga    60
ccctctcacc tgcgatgtaa accagaccct gttctctcta tagggagagt aatccattga    120
cacttctgtg tgtatgaatt atttaaatgt aatttagatt aataatttat gtgcgagtag    180
```

```
aaagagtgtt tattttgtta aaaggttcgt tttgaaaaac aaagatatgt gcgtcttgaa      240
caaccgctct attagccgtt tgttggctac aaatggcgta acataaaatt cgtttatttc      300
ttcgattctt tcttataaac agggctgtgg tactgggagc tcacaatttt ttttttacttt     360 tttttttat ttttgttctt tgttaatcat tttctttctg tttcttttac acgttacaga      420
ttgtaattat tggcattggt tttatacaaa gttgttggaa gtcccttt                    468

<210> SEQ ID NO 63
<211> LENGTH: 442
<212> TYPE: DNA
<213> ORGANISM: Halyomorpha halys

<400> SEQUENCE: 63
actgaagtat acggggacaa atcaagatca ttagggacaa ataagaagaa aaggagaaat       60
ctcggagttc cctacccggt aagcaccggc tccctcaatt tgacagttga aaccggcgga      120
gcaataacgt caccacgacc aaacttaagc cggaccccct taactgaatat aaagcaacgt     180 acattacttt tggactgggg ggtggtacca atcatatcca accgatagat gtctattggg      240
gggaggtata caaactttat ggttattttt tcagggattc cctacgaaga caacagacta     300
aaatgcttct taacttaacc gtgtgttttt tattttatt atagtgaact tttcatttta     360
tacagattta ataaaaaatt ctaattaa attaataata taaaacatta ttaatcatat       420
aaaacgtgaa agaaacaacg tt                                              442

<210> SEQ ID NO 64
<211> LENGTH: 539
<212> TYPE: DNA
<213> ORGANISM: Halyomorpha halys

<400> SEQUENCE: 64
acggtactgt ttacaatggg gatagtaaag ggtaatttgg atcaactttg gtacgatcag       60
actacattcc tgtaacactt tagtgaggaa agtgtacttt aagtaaccaa tggcatggta     120
tcttcagccg ctaggtgatt ccttctcatg aatataacac gtaaatgagc aaaagtgaaa     180
gacttgaaag ttgactgtga gtgtgttgac ctctctatct gttattttgg caaaattgtt     240 ataggagt attttatacg gaacggcttg gtgtccaacc cttggtgacg aaatcgactt       300
catagctaag gactatctta acttacttttt tatagttaaa aggttctcat agtttaattt     360
tcaccgttac gagttacttg attcggttac tcgttttttg tttttagtcc gtttgtatat     420
ctataaagac tataggtatt ggttatgaac tctgaacaag atcgattact gaattttttt     480
tctaatcact tcttagtcat tttttatagt cttaataacc taactttcat ggctatggt       539

<210> SEQ ID NO 65
<211> LENGTH: 465
<212> TYPE: DNA
<213> ORGANISM: Halyomorpha halys

<400> SEQUENCE: 65
aaaggaactt taactgccat ttgttaatga agttcttttc gattgctata cacaaggcaa       60
acacattcgt taagatgcaa caccatattt catcccccta tcctcccttc tcactttaaa     120
actcacggat aacttattcc ctatttagtg ttgataagtt aattcgtttt aaaatagttg     180
tattaaaaaa aaaaaaatta aatgttattt attagaaaac ctatcgcctc tgtattcatg     240
ttaattatat ttattagttg ccgcactagt cataggtaat gtttaaaaaa aaagcagatg     300
```

```
gtttactgtt aatgtaacta gtgtcgtcta tgttgtacat tttgtgacaa catggaatgt    360
acaaataaaa aaataatttt aatataatta attattatca ttacataaat atatataa     420 tatatatata aatgtgctaa atatacagca acatatttgc aatga                   465
```

<210> SEQ ID NO 66
<211> LENGTH: 498
<212> TYPE: DNA
<213> ORGANISM: Halyomorpha halys

<400> SEQUENCE: 66

```
atgatggcat attcggcatt acaatgtcac cccgagatat aactggccga aggtatttgt     60
tctttcatcc attatccagc ttccgagagt ttcatattga cacgatgatg cttcaaaacg    120
aaacttttgc taaaagagca gacgaaatga tgaaactatt gggtgaggag aggaggacgg    180
atcgaggaca tgctgctggc tcatcgatgg atagaaatgg agttctcttc tataacctaa    240 tatcccttc tgctgtaggg tgttggaact ctaggctgcc acattatcca gagactcaag     300
ggatagttga aacaaataat atcacactct cctttccaaa tgatttgaaa gttgacaagg    360
aacccattca aagattgtgg gttttgagta accgattgca ccgatatttg tattccaagc    420
ttgatccttc tgatgtgaat tttagggtaa tgacaatgcc tgtagatgaa gcagtgaaag    480
gtacgccttg tgacgatt                                                 498
```

<210> SEQ ID NO 67
<211> LENGTH: 512
<212> TYPE: DNA
<213> ORGANISM: Halyomorpha halys

<400> SEQUENCE: 67

```
ggcaattcag ggataggaca agtattggat atcctggacc ataagaattc agatttcagt     60
gattatgcta gttggaagaa caaagttgaa tacaaatcaa ggaatacaat gtgtgctttt    120
ccagtactgg gtcttctaca tgcaggactg acctgtaacg accttattca taaaactatg    180
gacatatttg gtgattatgg acttatgttt caagtatgga atgatttcat ggatttctat    240
tcagtgcaag aggaatctgg taaaggaaat tatgattgca agaacaatgt aaaaaactgg    300
gcaactataa cagcaatgac tcactttaat cccgcccaag ctaaagagtt cagggactgc    360
tatgggacca acgatccagc taaaagatct agagtacgcg aactgtttga cgagatagat    420
ttacccagga aatacttgga ttatttaagg aatatccgtg ttactgttga aaaaaaaatc    480
ggtgaactta gtgatgccag agtacgtgat gc                                 512
```

<210> SEQ ID NO 68
<211> LENGTH: 499
<212> TYPE: DNA
<213> ORGANISM: Halyomorpha halys

<400> SEQUENCE: 68

```
ggatgcttat gaataatcca gagctgtata caaatgtaaa tgcattgcaa aaacgcgatg     60
cacaagaggt cttggaagaa gttaaagatc tattaccatg gtctatagga gaaaacgtgc    120
tagatgttgg ctgtgaccct ggtgatctca catcctccct tctcacttca tatctggcca    180
atgactatcg agtggtcggt tgcgatattt ctgaagctat ggtgaaatat gctcaagcaa    240
aatatggaaa cgatcaattt tgtttcaaac agcttgatat cagcaatgga atatatggga    300
tgaactggga gaggagatt tttgataaag tattttcatt ttactgcctt cactgggtta    360
aagatcagat acaagcagca gaaaacattt atagtttgct gaaagatggt ggttatttg    420
```

```
tcacaatgtt cactatatct catccgtttc ttattctatt tagcagactt aaggaaaacc    480
caaaatggca atcctatac                                                  499
```

<210> SEQ ID NO 69
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 69

```
ttgatagttg tttggatttt gaaggt                                          26
```

<210> SEQ ID NO 70
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 70

```
tcttacttga tcagcgctca gaa                                             23
```

<210> SEQ ID NO 71
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 71

```
aactacctcg acgggatgat                                                 20
```

<210> SEQ ID NO 72
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 72

```
catatcacca ttgtgccttt gtc                                             23
```

<210> SEQ ID NO 73
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 73

```
ttgtttaaat gtaaccctac acagg                                           25
```

<210> SEQ ID NO 74
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 74

```
cacacaaact gatgtagatg aactc                                           25
```

<210> SEQ ID NO 75

```
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 75
agtcctttca tcccacaaa                                                19

<210> SEQ ID NO 76
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 76
ggatttaaga cagttgtgtt ctg                                           23

<210> SEQ ID NO 77
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 77
catatgtgcc cacagtgcct aa                                            22

<210> SEQ ID NO 78
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 78
ggcgatctta aaattggtag catt                                          24

<210> SEQ ID NO 79
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 79
agaaagacaa agaaaatgtg caatgt                                        26

<210> SEQ ID NO 80
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 80
acattccaaa aacagtttca acca                                          24

<210> SEQ ID NO 81
<211> LENGTH: 31
<212> TYPE: DNA
<213> ORGANISM: Artificial Sequence
<220> FEATURE:
<223> OTHER INFORMATION: Chemically Synthesized

<400> SEQUENCE: 81
```
cctcattcta cacaagagaa ctaatcaata g        31

<210> SEQ ID NO 82
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 82
gctctaaaga ggaaagaag aataaacag              29

<210> SEQ ID NO 83
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 83
tttcagcttc aatggtcaac aga                   23

<210> SEQ ID NO 84
<211> LENGTH: 27
<212> TYPE: DNA
<213> ORGANISM: Artificial Sequence
<220> FEATURE:
<223> OTHER INFORMATION: Chemically Sythesized

<400> SEQUENCE: 84
caactaggtt taatgggaaa tgatagg               27

<210> SEQ ID NO 85
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 85
gaaagaaatg aatgacggaa tcg                   23

<210> SEQ ID NO 86
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 86
tttgccttgt gtatagcaat cga                   23

<210> SEQ ID NO 87
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 87
cctggaatga tggcatattc g                     21

<210> SEQ ID NO 88
<211> LENGTH: 23
<212> TYPE: DNA

```
<213> ORGANISM: Artificial Sequence
<220> FEATURE:
<223> OTHER INFORMATION: Chemically Synthesized

<400> SEQUENCE: 88
tgaaactctc ggaagctgga taa                                              23

<210> SEQ ID NO 89
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 89
ctgttgaaaa aaaaatcggt gaact                                            25

<210> SEQ ID NO 90
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 90
tcaacattat gatttccgtc tccat                                            25

<210> SEQ ID NO 91
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 91
aggaaaaccc aaaatggcaa t                                                21

<210> SEQ ID NO 92
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 92
atgtattctt cttttggatc ttttcttgag                                       30

<210> SEQ ID NO 93
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 93 atgccccccgc ctgtccttat t                                               21

<210> SEQ ID NO 94
<211> LENGTH: 21
<212> TYPE: DNA
<213> ORGANISM: Artificial Sequence
<220> FEATURE:
<223> OTHER INFORMATION: Chemically Synthesized
```

```
<400> SEQUENCE: 94
tgaaagcagc ctgaatagtg g                                              21
```

DOUBLE STRAND RNA AS MOLECULAR BIOPESTICIDES FOR RNA INTERFERENCE THROUGH FEEDING IN THE HEMIPTERAN INVASIVE INSECT PEST, BROWN MARMORATED STINK BUG

CROSS-REFERENCE

The present application claims priority to U.S. Provisional Patent Application Ser. No. 62/366,237, filed on Jul. 25, 2016, the content of which is expressly incorporated herein by reference.

BACKGROUND OF THE INVENTION

Field of Invention

The present disclosure provides compositions and methods utilizing double strand ribonucleic acid (dsRNA) to control the insect pest, the brown marmorated stink bug (*Halyomorpha halys*). More particularly, the present invention relates to several specific synthetic dsRNAs that induce RNA interference (RNAi) in the target insect.

Background

Insect pests comprise a broad collection of animals that adversely affect urban and rural plants and animals. *Halyomorpha halys* (stål) (Heteroptera: Pentatomidae), commonly known as the brown marmorated stink bug (BMSB), is an invasive insect native to Asia (China, Taiwan, Korea, and Japan) that has emerged in the last decade as an important major insect pest in the United States, Canada and Europe. BMSB is a polyphagous piercing-sucking feeder causing damage by inserting their feeding stylets into the fruit, pods, buds, leaves, and stems of more than three hundred known plant hosts. This pest poses a considerable ecological and economic threat—billions of dollars annually—to specialty crops such as apples, stone and pome fruits, grapes, ornamental plants, vegetables, seed crops, as well as staple crops such as soybean and corn. BMSB has recently been found to be most abundant on extended fruiting plants such as sweet corn, okra, eggplant and bell pepper as these tend to support a longer life cycle (Zobel et al, J. Econ. Entomol., (2016)). BMSB has rapidly expanded its range from the original single point of accidental introduction and establishment in the Allentown, Pa. area in the late 1990s. Damage has been particularly extensive in the U.S. Mid-Atlantic Region (DE, MD, PA, NJ, VA, and WV) and has been detected in 42 states and Canada, as well as Europe (Xu et al, Biol. Invasions, (2014) 16:153-66; Leskey et al, Outlooks on Pest Management, (2012) 23(5):218-26; Hoebeke, Proc. Entomol. Soc. Wash., (2003) 105:225-37). In addition to being an agricultural pest, BMSB is also a nuisance pest because it invades indoor structures such as houses, schools and other indoor spaces that provide a safe hiding area in the fall to overwinter until spring for mating and egg laying (Leskey et al., supra). BMSB may trigger an immunological response in humans by causing allergic reactions leading to conjunctivitis and rhinitis in individuals sensitive to aeroallergens, or through contact dermatitis upon exposure to the crushed animal (Mertz et al, J. Allergy Clin. Immunol., (2012) 130(4):999-10001; Anderson et al, Dermatitis, (2012) 23(4): 170-72). As yet, no effective control methods have been discovered, leading us to investigate the possibility of using RNA-mediated interference (RNAi) as an approach to control this insect.

The discovery of RNA-mediated interference (RNAi) has facilitated research to understand gene function and regulation. RNAi is a well described gene regulatory mechanism wherein exogenous dsRNA is introduced into the cells of eukaryotic organisms and targets degradation of host cell mRNAs containing sequences complementary to the dsRNA (Mello and Conte, Nature (2004) 431:338-42). RNAi depletes host mRNA either by transcriptional gene silencing, or at a posttranscriptional level, thereby affecting translation of the protein (Ambros, Nature (2004) 431:350-55). RNAi takes advantage of internal cellular defenses against the presence of dsRNA, which typically indicates an on-going viral infection.

Virally induced dsRNA-activated innate immune responses in mammalian cells initiate a chain of events such as inhibition of protein synthesis, transcriptional induction of antiviral genes, and leading to cell death lead to the discovery of dsRNA mediated RNA interference (RNAi) (Barber, G. N., Cell Death and Differentiation, (2005) 12(6): 563-70; Gantier & Williams, Cytokine and Growth Factor Revs., (2007) 18(5-6):363-71). RNAi is a phenomenon of posttranscriptional gene silencing mediated by dsRNA or small interfering RNA siRNA. RNAi involves sequence specific degradation of a target gene mRNA mediated by dsRNA. These dsRNAs are subsequently cleaved to 19-21 bp siRNAs fragments by member of the RNase III superfamily of bidentate nucleases known as dicers (Bernstein et al, Nature, (2001) 409(6818):363-66; Ketting et al, Genes & Develop., (2001) 15(20):2654-59). These short RNAs unwind and together with a multi protein complex, RNA-induced silencing complex (RISC) and acts as template for complementary mRNA recognition. This RISC-RNA complex in conjunction with argonaute multi-domain protein containing an RNAse H like domain are corollary for target degradation hence silencing the gene resulting in translational blockage (Martinez et al, Cell, (2002) 110(5):563-74; Bartel, D. P., Cell, (2004) 116(2):281-297).

RNAi was first discovered in the nematode *Caenorhabditis elegans* (Fire et al, Nature, (1998) 391(6669):806-11). Since the inception of RNAi as an efficient method of gene silencing, it has been successfully applied in insects for dsRNA-mediated gene regulation. dsRNA delivery system to insects and insect cells included feeding (Baum et al, Nature Biotech., (2007) 25(11):1322-26; Timmons & Fire, Nature, (1998)395(6705):854), soaking (Saleh et al, Nature Cell Biol., (2006) 8(8):793-802), microinjections (Amdam et al, BMC Biotech., (2003) 3:1), and other techniques (reviewed in Huvenne & Smagghe, J. Insect Physiol., (2010) 56(3):227-35) were used for systemic dsRNA uptake. To date, RNAi technology has been successfully applied to hemipteran insects indicating depletion of calreticulin and cathepsin-L (Jaubert-Possamai et al, BMC Biotech., (2007) 7:63), Coo2 (Mutti et al., J. Insect Sci., (2006) 6:1-7), ApAQP1 of insect aquaporins (Shakesby et al, Insect Biochem. Mol. Biol., (2009) 39(1):1-10) and hunchback (Mao & Zeng, PLoS One, (2012) 7(11): e48718) in the pea aphid (*Acyrthosiphon pisum*) by mechanical microinjection, or through artificial diets. A recent report demonstrated depletion of the catalase gene in BMSB utilizing mechanical microinjection as a mode of dsRNA delivery. But they also raised a concern alongside that mechanical puncture may stress the animals that may induce unexpected variations in the expression of the housekeeping genes affecting validation of RNAi through qRT-PCR (Bansal et al, PLoS One, (2016) 11(5):e0152730).

Reported herein are compositions and methods for controlling The depletion of putative genes varied in diminishing the target mRNA but higher concentrations of dsRNA were required for depletion of certain genes, including HP C37491, AK, Ftz F1 and JH. Vitellogenin, the major egg yolk protein displayed a significant reduction with a gradual increase in dsRNA concentration but was hyperexpressed at the peak concentration. The importance and correlation in the sesquiterpene biosynthesis pathway was also investigated where depletion of JH negatively affected the expression of FPPS1, an enzyme important in synthesis of the male aggregation pheromone. Here we have demonstrated that exogenously synthesized dsRNA can elicit RNAi response in BMSB through an oral delivery method. This efficient vegetable-mediated dsRNA delivery method suggested that this RNAi pathway might be directed for the control of invasive insect pests of agriculture.

SUMMARY OF THE INVENTION

In one embodiment, the present disclosure provides a double-stranded ribonucleic acid (dsRNA) comprising a sense region with at least 95% sequence identity to any one of the sequences provided herein, for example SEQ ID NOs: 56, 66, 67, or 68, and an antisense region comprising a second sequence complementary to the sense region. In particular embodiments, the sense region has at least 99% or 100% sequence identity to any one of SEQ ID NOs: 56, 66, 67, or 68. In other embodiments, the sense region comprises the precise sequence provided as SEQ ID NO: 56, SEQ ID NO: 66, SEQ ID NO: 67, or SEQ ID NO: 68. dsRNAs of the present invention can be expressed in a plant cell or distributed throughout at least part of a living plant material's vascular tissues. In some embodiments, the living plant material is a fruit, vegetable, stem or leaf. In other embodiments a dsRNA of the present invention is expressed in a bacterial or yeast cell. In still other embodiments, a dsRNA of the present invention can also comprise a T7 RNA polymerase promoter sequence.

In another embodiment, the present disclosure provides a dsRNA comprising a sense region comprising a sequence with at least 95% sequence identity to a portion of at least 19 consecutive nucleotides of any one of the sequences provided herein, for example SEQ ID NOs: 56, 66, 67, or 68, and an antisense region comprising a second sequence complementary to the sense region. dsRNAs of the present invention can be expressed in a plant cell or distributed throughout at least part of a living plant material's vascular tissues. In some embodiments, the living plant material is a fruit, vegetable, stem or leaf. In other embodiments a dsRNA of the present invention is expressed in a bacterial or yeast cell.

In yet another embodiment, the present disclosure provides a DNA molecule comprising a promoter functional in a host cell and a DNA encoding a dsRNA comprising a first region and a second region, wherein the first region comprises a sense region with at least 95% sequence identity to SEQ ID NOs: 56, 66, 67, or 68 and a second region complementary to the first region. The host cell can be a bacterial cell, a yeast cell or a plant cell. The present disclosure also provides host cells containing such DNA molecules, as well as non-transgenic living plant material, transgenic plant cells, transgenic plants and transgenic seeds containing any of the dsRNA species disclosed herein.

Further provided herein are methods of controlling *H. halys* comprising applying one or more dsRNA molecules of the present invention to a living plant material such that the one or more dsRNA molecules are taken up and distributed by the vascular tissue of the living plant material and allowing the one or more insects to ingest an effective amount of the one or more dsRNA molecules, thereby controlling the one or more insects. In a particular embodiment, the one or more dsRNA molecules comprise a first dsRNA molecule and a second dsRNA molecule, wherein the first dsRNA molecule comprises a sense region with at least 95% sequence identity to SEQ ID NO: 56 and an antisense region comprising a second sequence complementary to the sense region and wherein the second dsRNA molecule comprises a sense region with at least 95% sequence identity to SEQ ID NO: 68 and an antisense region comprising a second sequence complementary to the sense region.

An additional method of controlling *H. halys* is provided herein. This method includes planting or growing a transgenic plant expressing one or more dsRNA molecules disclosed herein and allowing one or more insects to ingest an effective amount of the one or more dsRNA molecules, thereby controlling the one or more insects. In a particular embodiment of this method, the one or more dsRNA molecules comprise a first dsRNA molecule and a second dsRNA molecule, wherein the first dsRNA molecule comprises a sense region with at least 95% sequence identity to SEQ ID NO: 56 and an antisense region comprising a second sequence complementary to the sense region and wherein the second dsRNA molecule comprises a sense region with at least 95% sequence identity to SEQ ID NO: 68 and an antisense region comprising a second sequence complementary to the sense region.

Still another embodiment of the present invention is a method of controlling *H. halys* including the steps of: a) providing a living plant material containing at least one double-strand RNA (dsRNA) wherein the at least one dsRNA molecule comprises a sense region with at least 95% sequence identity to SEQ ID NOs: 56, 66, 67, or 68 and an antisense region comprising a second sequence complementary to the sense region, wherein the at least one dsRNA molecule is distributed throughout at least part of the living plant material's vascular tissues and wherein the living plant material does not contain genetic information allowing for the production of the at least one double strand dsRNA molecule; b) allowing the insect to ingest a sufficient amount of the at least one dsRNA molecule, by feeding on the plant material, to interfere with the production of at least one protein targeted by the at least one dsRNA molecule, thereby inducing RNAi in the insect, and; c) controlling the insect via RNAi. In some embodiments, the living plant material is a fruit, vegetable, stem or leaf. In a specific embodiment, the living plant material is a green bean. In some embodiments, the at least one dsRNA molecule comprises two dsRNA molecules wherein the first dsRNA molecule comprises a sense region with at least 95% sequence identity to SEQ ID NO: 56 and an antisense region comprising a second sequence complementary to the sense region and wherein the second dsRNA molecule comprises a sense region with at least 95% sequence identity to SEQ ID NO: 68 and an antisense region comprising a second sequence complementary to the sense region.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The patent application file contains at least one drawing executed in color. Copies of this patent or patent application publication with color drawing(s) will be provided by the Office upon request and payment of the necessary fee.

The novel features of the invention are set forth with particularity in the claims. Features and advantages of the present invention are referred to in the following detailed description, and the accompanying drawings of which:

FIG. 1A: Organic green beans were washed with sodium hypochlorite and trimmed from the calyx end to a total length of 3 inches. These beans were then immersed in ddH$_2$O or ddH$_2$O solution with green food color for a period of 3 hrs. Transport of green food color was observed in the green bean encircled by the oval area at the exposed calyx. FIG. 1B: BMSB feeding bioassay. Three animals were placed in a magenta jars with 3 greens beans immersed in either 2 ml microcentrifuge containing ddH$_2$O or a solution of ddH$_2$O and green food color. FIG. 1C: BMSB placed in the magenta jars are able to pierce through the green beans and reach the diet with their stylets. FIG. 1D: BMSB frass observed on day 2 and 3 of ingesting a solution of ddH$_2$O and green food color through green beans.

FIGS. 6A-6D provide depictions of RNAi mediated depletion of sesquiterpenoid-producing proteins farnesyl diphosphate synthase (FPPS1) and juvenile hormone (JH). Total RNA from the entire BMSB nymphs fed on green bean mediated dsRNA for: (FIG. 6A) RNAi of FPPS1 using 5 μg dsRNA diet, (FIG. 6B) RNAi of JH using 5 μg dsRNA diet, (FIG. 6C) RNAi of JH using 10 μg dsRNA diet, and (FIG. 6D) RNAi of JH using 20 μg dsRNA diet was isolated and the levels of transcripts were measured by qPCR. LacZ RNAi (Mock) served as control. 18s RNA was used as an internal standard to correct for differences in RNA recovery from tissues. Results are from three biological replicates and error bars indicate ±SEM.

FIGS. 7A-7C provide graphs depicting Evaluation of the effects of combinatorial dsRNA-mediated RNAi on gene regulation. qPCR analysis of JH and FPPS1 expression following individual or a combined RNAi. BMSB 4$^{th}$ instar nymphs were fed on diets containing dsRNA for FPPS1, JH or in combination and the total RNA was isolated and evaluated. The concentrations of dsRNA fed through the green bean delivery method were FPPS1 (5 μg), JH (5 μg or 20 μg) and a combination containing a constant amount of FPPS1 (5 μg) and either 5 μg or 20 μg of JH. (FIG. 7A) Expression level of JH transcript in 5 μg JH dsRNA diet, (FIG. 7B) Expression level of JH transcript in 20 μg JH dsRNA diet, and (FIG. 7C) Expression level of FPPS1 transcript in 5 μg JH dsRNA diet. LacZ RNAi (Mock) served as control. 18s RNA was used as an internal standard to correct for differences in RNA recovery from tissues. Results are from three biological replicates and error bars indicate ±SEM.

FIGS. 8A-8B provide pictorial and graphic depictions of the effects of RNAi on the development of BMSB. Five 4$^{th}$ instar nymphs were fed on in vitro transcribed dsRNA indicated here as LacZ RNAi (Mock), FPPS1, JHAMT, Vg, and a combination of either FPPS1+JHAMT or JHAMT+Vg for a period of 5 days following which the larvae were moved to an organic green bean diet. As a control green beans were immersed in RNase/DNAse free water. FIG. 8A: Images were taken 5 days subsequent to stopping per os of feeding of dsRNA. Mock treated (panel a) molted to an adult female, JH treated (panel b), and JH+FPPS1 treated (panel c) died on day 13 (8 days subsequent to stopping per os of feeding of dsRNA). All images were measured to scale of 1 cm as indicated in panel c. FIG. 8B: A comparison between RNAi depletion of specific gene targets to the body mass was measured from the first day of dsRNA feeding (indicated here day 0). Results are from five biological replicates normalized to the controls and error bars indicate ±SEM. A one way analysis of variance (ANOVA) was performed to test for statistical significance of data that indicate significant differences at P value of 0.00047.

Figure 1A:
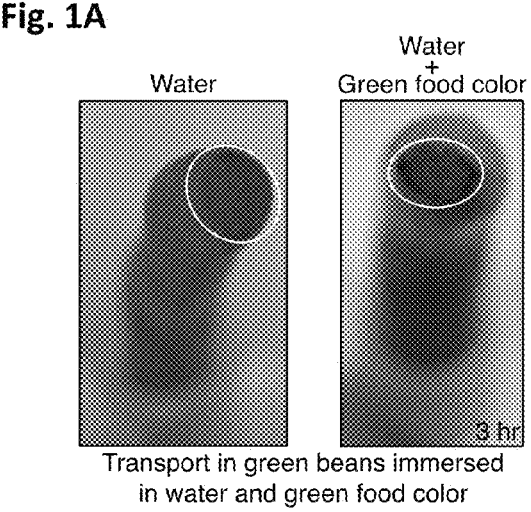
FIGS. 1A-1D provide pictorial depictions of delivery of nutrients through green beans.

BMSB adult males were fed on in vitro transcribed dsRNA indicated here as Mock (LacZ), FPPS1 and JHAMT dsRNAs for a period of 5 days following which sesquiterpene emissions of males subjected to different treatments were compared. The GC peak areas of (3S,6S,7R,10S)-10,11-epoxy-1-bisabolen-3-ol, the male-specific aggregation pheromone of the brown marmorated stink bug were compared for a period of 21 days. Results are normalized to the controls and error bars indicate ±SEM [n=4 (control), n=6 (mock and FPPS1)]. A one way analysis of variance (ANOVA) was performed to test for statistical significance of data that indicate significant differences at P value of 0.00068 and *0.00047.

DETAILED DESCRIPTION OF THE INVENTION

RNA interference (RNAi) is a double stranded RNA (dsRNA) or small interfering RNA (siRNA) mediated gene-silencing mechanism that exists in animals and plants. RNAi has become a useful technology for functional gene regulation and provides a potential tool for development of bio-molecular pesticides. Described herein, molecular biopesticides detrimental to *Halyomorpha halys* (stål) (Heteroptera: Pentatomidae), the brown marmorated stink bug (BMSB), were generated from in vitro transcribed double stranded RNAs (dsRNAs) designed for specific gene sequences to selectively trigger the RNA interference (RNAi) response. Although most RNAi studies in insects to date have relied on mechanical microinjection to deliver dsRNA(s), to be economically and practically useful in the environment as molecular biopesticides, dsRNA(s) are preferably orally delivered.

BMSB, which is a polyphagous piercing-sucking insect, feeds on vegetable phloem by piercing the plant with its stylet mouthparts and sucking and ingesting plant fluids mediated by turgor pressure. Provided herein are methods and compositions for providing dsRNAs capable of controlling insect pests, particularly by feeding. In some embodiments, dsRNA species targeting a pest can be delivered to the animals using a newly developed delivery method entailing green beans immersed in an aqueous solution of dsRNA in which the dsRNAs have been distributed through the vascular system. Alternately, the dsRNA species disclosed herein can be expressed in transgenic plants that would be targeted by BMSB, thus allowing the insect pest to uptake the controlling dsRNA by feeding.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

Definitions

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means from a range of 0.9 g to 1.1 g and all values within that range, whether specifically stated or not.

The term "gene" refers to a DNA sequence involved in producing a RNA or polypeptide or precursor thereof. The polypeptide or RNA can be encoded by a full-length coding sequence or by intron-interrupted portions of the coding sequence, such as exon sequences.

The term "oligonucleotide" refers to a molecule comprising a plurality of deoxyribonucleotides or ribonucleotides. Oligonucleotides may be generated in any manner known in the art, including chemical synthesis, DNA replication, reverse transcription, polymerase chain reaction, or a combination thereof. In one embodiment, the present invention embodies utilizing the oligonucleotide in the form of dsRNA as means of interfering with a critical developmental or reproductive process that leads to control. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

The term "a nucleic acid consisting essentially of", and grammatical variations thereof, means nucleic acids that differ from a reference nucleic acid sequence by 20 or fewer nucleic acid residues and also perform the function of the reference nucleic acid sequence. Such variants include sequences which are shorter or longer than the reference nucleic acid sequence, have different residues at particular positions, or a combination thereof.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide, which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

As used herein, "dsRNA" refers to double-stranded RNA that comprises a sense and an antisense portion of a selected target gene (or sequences with high sequence identity thereto so that gene silencing can occur), as well as any smaller double-stranded RNAs formed therefrom by RNAse or dicer activity. Such dsRNA can include portions of single-stranded RNA, but contains at least 19 nucleotides double-stranded RNA. In one embodiment of the invention, a dsRNA comprises a hairpin RNA which contains a loop or spacer sequence between the sense and antisense sequences of the gene targeted, preferably such hairpin RNA spacer region contains an intron, particularly the rolA gene intron (Pandolfini et al., 2003, BioMedCentral (BMC) Biotechnology 3:7 (www.biomedcentral.com/1472-6750/3/7)), the dual orientation introns from pHellsgate 11 or 12 (see WO 02/059294 and SEQ ID NO: 25 and 15 therein) or the pdk intron (*Flaveria trinervia* pyruvate orthophosphate dikinase intron 2; see WO99/53050).

Included in this definition are "siRNAs" or small interfering (double-stranded) RNA molecules of 16-30 bp, 19-28 bp, or 21-26 bp, e.g., such as the RNA forms that can be created by RNAseIII or dicer activity from longer dsRNA. siRNAs as used herein include any double-stranded RNA of 19 to 26, or 21 to 24 basepairs that can interfere with gene expression when present in a cell wherein such gene is expressed. siRNA can be synthetically made, expressed and secreted directly from a transformed cell or can be generated from a longer dsRNA by enzymatic activity. These siRNAs can be blunt-ended or can have overlapping ends. Also, modified microRNAs comprising a portion of a target gene and its complementary sequence are included herein as dsRNAs.

The term "chimeric" when referring to a gene or DNA sequence is used to refer to a gene or DNA sequence comprising at least two functionally relevant DNA fragments (such as promoter, 5'UTR, coding region, 3'UTR, intron) that are not naturally associated with each other, such as a fusion of functionally relevant DNA fragments from different sources to form an expressible chimeric gene expressing a dsRNA targeting a *H. halys*.

Sequences or parts of sequences which have "high sequence identity", as used herein, refers to the number of positions with identical nucleotides divided by the number of nucleotides in the shorter of the sequences, being higher than 95%, higher than 96%, higher than 97%, higher than 98%, higher than 99%, or between 96% and 100%. A target gene, or at least a part thereof, as used herein, preferably has high sequence identity to the dsRNA of the invention in order for efficient gene silencing to take place in the target pest. Identity in sequence of the dsRNA or siRNA with a part of the target gene RNA is included in the current invention but is not necessary.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wis., USA) using the default scoring matrix with a gap creation penalty of 50 and a gap extension penalty of 3.

For the purpose of the invention, the "complement of a nucleotide sequence X" is the nucleotide sequence which would be capable of forming a double-stranded DNA or RNA molecule with the represented nucleotide sequence, and which can be derived from the represented nucleotide sequence by replacing the nucleotides by their complementary nucleotide according to Chargaff's rules (A<>T; G<>C; A<>U) and reading in the 5' to 3' direction, i.e., in opposite direction of the represented nucleotide sequence.

A dsRNA "targeting" a gene, mRNA or protein, as used herein, refers to a dsRNA that is designed to be identical to, or have high sequence identity to, one or more mRNAs endogenous to the target organism (the target genes), and as such is designed to silence such gene upon application to such insect. One dsRNA can target one or several homologous target genes in one insect or one or several homologous target genes in different insects which can feed on the same host plant. One of skill in the art will recognize that multiple currently-known genes, as well as other currently unknown or uncharacterized genes can be targeted by applying the teachings herein.

"Insecticidal activity" of a dsRNA, as used herein, refers to the capacity to obtain mortality in insects when such dsRNA is fed to insects, which mortality is significantly higher than a negative control (using a non-insect dsRNA or buffer).

"Insect-control" using a dsRNA, as used herein, refers to the capacity to inhibit the insect development, fertility, inhibition of pheromone production, or growth in such a manner that the insect population provides less damage to a plant, produces fewer offspring, are less fit or are more susceptible to predator attack, or that insects are even deterred from feeding on such plant.

As used herein, the term "LacZ dsRNA" refers to a control dsRNA construct targeting a LacZ sequence. The LacZ protein (lacZ) is commonly used as a reporter gene in prokaryotic systems.

The term "corresponds to" as used herein means a polynucleotide sequence homologous to all or a portion of a reference polynucleotide sequence, or a polypeptide sequence that is identical to a reference polypeptide sequence. In contradistinction, the term "complementary to" is used herein to mean that the complementary sequence is homologous to all or a portion of a reference polynucleotide sequence. For example, the nucleotide sequence "TATAC" corresponds to a reference sequence "TATAC" and is complementary to a reference sequence "GTATA". An "RNA from" of a DNA sequence, as used herein is the RNA sequence of said DNA, so the same sequence but wherein the T nucleotide is replaced by a U nucleotide.

An "effective amount" is an amount sufficient to effect desired beneficial or deleterious results. An effective amount can be administered in one or more administrations. In terms of treatment, an "effective amount" is that amount sufficient to make the target pest non-functional by causing an adverse effect on that pest, including (but not limited to) physiological damage to the pest; inhibition or modulation of pest growth; inhibition or modulation of pest reproduction; or death of the pest. In one embodiment of the invention, a dsRNA containing solution is fed to a target insect wherein critical developmental and/or reproductive functions of said insect are disrupted as a result of ingestion.

General Overview

Double-stranded RNA (dsRNA) mediated gene silencing, also known as RNA interference (RNAi), is a breakthrough technology for functional genomic studies providing a potential tool for management of insect pests. Since the inception of RNAi numerous studies have documented successful introduction of synthetic dsRNA or siRNA into the organism that triggers a highly efficient gene silencing through degradation of endogenous RNA homologous to the presented dsRNA/siRNA. One focus of the present invention is providing for RNAi-mediated control of the brown marmorated stink bug (BMSB, *Halyomorpha halys*).

The BMSB, a hemipteran insect, is an invasive agricultural pest in North America. The significance of its spread has affected both the rural and urban areas especially the agricultural and specialty crops. RNAi technology can serve as a viable tool for control and management of this voracious pest, however, the major obstacle to utilizing RNAi approaches is the challenge of delivery of effective dsRNA to the insect. Mechanical microinjection of dsRNAs and soaking in ddH$_2$O, or other liquid, containing dsRNA(s) are both methods that have been successfully utilized for dsRNA delivery have been documented to elicit an effective RNAi response in laboratory studies of RNAi in insects. These techniques, however, are impracticable in an agricultural setting. One approach that can be used to induce RNAi via feeding is to construct transgenic plants expressing dsRNA species targeting insect pests important to that particular plant (see, e.g., PCT Appl. No. WO2001037654).

To be relevant for agricultural pest control, delivery of dsRNA to insect pests should be economical, efficient and advantageous for the agriculture community. dsRNA delivered through ingestion of its solution directly (Baum et al., supra), by feeding bacteria expressing dsRNA (Timmons and Fire, Nature, (1998) 395:854), or via a dsRNA-containing diet are other possible strategies for inducing RNAi as an agricultural pest control methodology. The compositions and methodologies disclosed herein can utilize any of these routes, as well as the use of "dsRNA traps" (vegetables, fruits, or other plant parts laden with the relevant dsRNA).

Double-stranded RNA and RNA Interference

Since its inception, RNAi has proved to be a potent tool to study gene function and regulation. With the advent of bioinformatics coupled with next-generation high throughput sequencing has unveiled an array of transcriptomic data available for a wide range of species at different stages of development and tissues. To attain an effective RNAi response in the biocontrol of pests, an accurate and precise mode of dsRNA delivery, efficient uptake and dsRNA stability are of utmost consideration.

Preferably, the dsRNAs to be used in this invention target at least one insect pest gene portion of at least 19 consecutive nucleotides occurring in identical sequence or with high sequence identity in the one or more target insects. In preferred embodiments of this invention, such dsRNAs do not silence genes of a plant host, or of other non-target animals, such as beneficial insects (e.g., pollinators), insect predators or animals such as reptiles, amphibians, birds, or mammals. Levels of homology between sequences of interest can be analyzed in available databases, e.g., by a BLAST search (see also www.ncbi.nlm.nih.gov/BLAST) or by hybridization with existing DNA libraries of representative non-target organisms. In one embodiment of this invention, the dsRNA or siRNA of the invention corresponds to an exon in a target gene.

As used herein, nucleotide sequences of RNA molecules can be identified by reference to DNA nucleotide sequences of the sequence listing. However, the person skilled in the art will understand whether RNA or DNA is meant depending on the context. Furthermore, the nucleotide sequence is identical between the types of polynucleotides except that the T-base is replaced by uracil (U) in RNA molecules.

In some embodiments, the length of the first (e.g., sense) and second (e.g., antisense) nucleotide sequences of the dsRNA molecules of the invention can vary from about 10 nucleotides (nt) up to a length equaling the length in nucleotides of the transcript of the target gene. The length of the first or second nucleotide sequence of the dsRNA of the invention can be at least 15 nt, or at least about 20 nt, or at least about 50 nt, or at least about 100 nt, or at least about 150 nt, or at least about 200 nt, or at least about 400 nt, or at least about 500 nt. If not all nucleotides in a target gene sequence are known, it is preferred to use such portion for which the sequence is known and which meets other beneficial requirements of the invention.

It will be appreciated that the longer the total length of the first (sense) nucleotide sequence in the dsRNA of the invention is, the less stringent the requirements for sequence identity between the total sense nucleotide sequence and the corresponding sequence in the target gene becomes. The total first nucleotide sequence can have a sequence identity of at least about 75% with the corresponding target sequence, but higher sequence identity can also be used such as at least about 80%, at least about 85%, at least about 90%, at least about 95%, about 100%. The first nucleotide sequence can also be identical to the corresponding part of the target gene. However, it is advised that the first nucleotide sequence includes a sequence of 19 or 20, or about 19 or about 20 consecutive nucleotides, or even of about 50 consecutive nucleotides, or about consecutive 100 nucleotides, or about 150 consecutive nucleotides with only one mismatch, preferably with 100% sequence identity, to the corresponding part of the target gene. For calculating the sequence identity and designing the corresponding first nucleotide sequence, the number of gaps should be minimized, particularly for the shorter sense sequences.

The length of the second (antisense) nucleotide sequence in the dsRNA of the invention is largely determined by the length of the first (sense) nucleotide sequence, and may correspond to the length of the latter sequence. However, it is possible to use an antisense sequence which differs in length by about 10% without any difficulties. Similarly, the nucleotide sequence of the antisense region is largely determined by the nucleotide sequence of the sense region, and may be identical to the complement of the nucleotide sequence of the sense region. Particularly with longer antisense regions, it is however possible to use antisense sequences with lower sequence identity to the complement of the sense nucleotide sequence, such as at least about 75% sequence identity, or least about 80%, or at least about 85%, more particularly with at least about 90% sequence identity, or at least about 95% sequence to the complement of the sense nucleotide sequence. Nevertheless, it is advised that the antisense nucleotide sequence always includes a sequence of 19 or 20, about 19 or about 20 consecutive nucleotides, although longer stretches of consecutive nucleotides such as about 50 nucleotide, or about 100 nucleotides, or about 150 nucleotides with no more than one mismatch, preferably with 100% sequence identity, to the complement of a corresponding part of the sense nucleotide sequence can also be used. Again, the number of gaps should be minimized, particularly for the shorter (19 to 50 nucleotides) antisense sequences.

In one embodiment of the invention, a dsRNA molecule may further comprise one or more regions having at least 94%, at least 95%, at least 96%, at least 97%, at least 98%, or at least 99%, sequence identity to regions of at least 19 consecutive nucleotides from the sense nucleotide sequence of the target gene, different from the at least 19 consecutive nucleotides as defined in the first region, and one or more regions having at least 94%, at least 95%, at least 96%, at least 97%, at least 98%, or at least 99%, sequence identity to at least 19 consecutive nucleotides from the complement of the sense nucleotide sequence of the target gene, different from the at least 19 consecutive nucleotides as defined in the second region, wherein these additional regions can base-pair amongst themselves.

Transgenic Plants and Plant Cells

One embodiment of the present invention provides a plant or cell comprising one or more inhibitory dsRNAs specific for one or more mRNAs of one or more *H. halys* genes. Inhibitory RNAs specific for one or more mRNAs means that the inhibitory RNA down-regulates the expression, or translation, of a specific mRNA. The inhibitory RNA can be single- or double-stranded or a combination thereof. For example, the present disclosure provides transgenic plants that express one or more inhibitory RNAs that down regulate expression, or translation, of one or more target genes when the one or more inhibitory RNAs are absorbed or ingested by a target insect (e.g., *H. halys*).

Another embodiment provides a transgenic plant that comprises inhibitory RNA that down regulates 3, 4, 5, 6, 7, 8, 9, 10, 11, 12, 13, 14, 15, 16, 17, 18, 19, 20, or more *H. halys* genes. Thus, the present disclosure provides transgenic plants and transgenic plant material that are resistant to disease caused by *H. halys*.

Another embodiment provides a transgenic plant or transgenic cell containing or expressing one or more inhibitory nucleic acids specific for at least a portion of a nucleic acid encoding one or more *H. halys* genes. The inhibitory nucleic acid is typically a small inhibitory RNA or microRNA that is specific for mRNA encoding a *H. halys* gene involved in growth, general health, fecundity, or reproduction. In some instances, the function of the target gene (or the protein encoded by the gene) is not known.

It will be appreciated by one of skill in the art that an inhibitory nucleic acid can be RNA, DNA, or a combination thereof. Additionally, the inhibitory nucleic acid can be single or multi-stranded and can be anti-sense or enzymatic. In one embodiment, an inhibitory nucleic acid interferes with, inhibits, or reduces the translation of a target mRNA. For example, an inhibitory nucleic acid can bind to a target mRNA and induce or promote the degradation of the target mRNA or physically prevent the cellular translational machinery from translating the target mRNA into a functional protein.

In some embodiments, a dsRNA chimeric gene, encoding a dsRNA targeting any of the genes disclosed herein, can be stably inserted in a conventional manner into the genome of a single plant cell, and the so-transformed plant cell can be used in a conventional manner to produce a transformed (i.e., transgenic) plant that has increased insect resistance. In this regard, a disarmed Ti-plasmid, containing the dsRNA chimeric gene, in *Agrobacterium tumefaciens* can be used to transform the plant cell, and thereafter, a transformed plant can be regenerated from the transformed plant cell using the procedures described in the art, for example, in EP 0116718, EP 0270822, PCT publication WO 84/02913 and published European Patent application ("EP") 0242246. Preferred Ti-plasmid vectors each contain the dsRNA chimeric gene between the border sequences, or at least located to the left of the right border sequence, of the T-DNA of the Ti-plasmid. Of course, other types of vectors can be used to transform the plant cell, using procedures such as direct gene transfer (as described, for example in EP 0233247), pollen mediated transformation (as described, for example in EP 0270356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (e.g., U.S. Pat. No. 6,140,553; Fromm et al., Bio/Technology (1990) 8, 833-839); Gordon-Kamm et al., The Plant Cell, (1990) 2, 603-618) and rice (Shimamoto et al., Nature, (1989) 338, 274-276; Datta et al., Bio/Technology, (1990) 8, 736-740) and the method for transforming monocots generally (PCT publication WO 92/09696). For cotton transformation, the method described in PCT patent publication WO 00/71733 can be used. For soybean transformation, reference is made to methods known in the art, e.g., Hinchee et al. (Bio/Technology, (1988) 6, 915) and Christou et al. (Trends Biotech, (1990) 8, 145) or the method of WO 00/42207.

The resulting transgenic plant can be used in a conventional plant breeding scheme to produce more transgenic plants with the same characteristics, or to introduce the dsRNA chimeric gene in other varieties of the same or related plant species. Seeds, which are obtained from the transformed plants, contain the dsRNA gene as a stable genomic insert. Plants comprising a dsRNA in accordance with the invention include plants comprising, or derived from, root stocks of plants comprising the dsRNA chimeric gene of the invention, e.g., fruit trees or ornamental plants. Hence, any non-transgenic grafted plant parts inserted on a transformed plant or plant part are included in the invention since the RNA interference signal is transported to these grafted parts and any insects feeding on such grafted plant are similarly affected by the dsRNA or siRNA of the invention.

A DNA encoding a dsRNA is typically inserted in a plant cell genome so that this DNA is downstream (i.e., 3') of, and operably linked to, a plant-expressible promoter which can direct expression in plant cells. This is preferably accomplished by inserting a dsRNA chimeric gene into the plant cell genome, particularly in the nuclear or plastid (e.g., chloroplast) genome. Also, in a dsRNA chimeric gene of the invention a nuclear localization signal can be added as described in published US patent application 20030180945.

A 'plant-expressible promoter' as used herein refers to a promoter that ensures expression of a dsRNA of the invention in a plant cell. Examples of promoters directing constitutive expression in plants are known in the art and include: the strong constitutive 35S promoters (the "35S promoters") of the cauliflower mosaic virus (CaMV), e.g., of isolates CM 1841 (Gardner et al., Nucleic Acids Res, (1981) 9, 2871-2887), CabbB-S (Franck et al., Cell (1980) 21, 285-294) and CabbB-JI (Hull and Howell, Virology, (1987) 86, 482-493); promoters from the ubiquitin family (e.g., the maize ubiquitin promoter of Christensen et al., Plant Mol Biol, (1992) 18, 675-689), the gos2 promoter (de Pater et al., The Plant J (1992) 2, 834-844), the emu promoter (Last et al., Theor Appl Genet, (1990) 81, 581-588), actin promoters such as the promoter described by An et al. (The Plant J, (1996) 10, 107), the rice actin promoter described by Zhang et al. (The Plant Cell, (1991) 3, 1155-1165); promoters of the Cassava vein mosaic virus (WO 97/48819, Verdaguer et al. (Plant Mol Biol, (1998) 37, 1055-1067), the pPLEX series of promoters from Subterranean Clover Stunt Virus (WO 96/06932, particularly the S4 or S7 promoter), an alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., EMBO J, (1984) 3, 2723-2730).

Alternatively, a plant-expressible promoter can be a tissue-specific promoter, i.e., a promoter directing a higher level of expression in some cells or tissues of the plant, e.g., in green tissues (such as the promoter of the PEP carboxylase). The plant PEP carboxylase promoter (Pathirana et al., Plant J, (1997) 12:293-304) has been described to be a strong promoter for expression in vascular tissue and is useful in one embodiment of the current invention. Alternatively, a plant-expressible promoter can also be a wound-inducible promoter, such as the promoter of the pea cell wall invertase gene (Zhang et al., Plant Physiol, (1996) 112:1111-1117). A 'wound-inducible' promoter as used herein means that upon wounding of the plant, either mechanically or by insect feeding, expression of the coding sequence under control of the promoter is significantly increased in such plant. These plant-expressible promoters can be combined with enhancer elements, they can be combined with minimal promoter elements, or can comprise repeated elements to ensure the expression profile desired.

Elements which can be used to increase expression in plant cells can be: an intron at the 5' end or 3' end of the chimeric gene, or in the coding sequence of the chimeric dsRNA gene (such as between the region encoding the sense and antisense portion of the dsRNA), e.g., the hsp70 intron, besides promoter enhancer elements, duplicated or triplicated promoter regions, 5' leader sequences different from another transgene or different from an endogenous (plant host) gene leader sequence, 3' trailer sequences different from another transgene used in the same plant or different from an endogenous (plant host) trailer sequence.

A dsRNA chimeric gene of the present invention can be inserted in a plant genome so that the inserted gene part is upstream (i.e., 5') of suitable 3' end transcription regulation signals (i.e., transcript formation and polyadenylation signals). This is preferably accomplished by inserting the dsRNA chimeric gene in the plant cell genome. Preferred polyadenylation and transcript formation signals include those of the nopaline synthase gene (Depicker et al., J. Molec Appl Gen, (1982) 1, 561-573), the octopine synthase gene (Gielen et al., EMBO J, (1984) 3:835-845), the SCSV or the Malic enzyme terminators (Schunmann et al., Plant Funct Biol, (2003) 30:453-460), and the T-DNA gene 7 (Velten and Schell, Nucleic Acids Res, (1985) 13, 6981-6998), which act as 3'-untranslated DNA sequences in transformed plant cells.

A dsRNA chimeric gene of the present invention can optionally be inserted in a plant genome as a hybrid gene, containing several dsRNA regions which target different genes. For example, a dsRNA chimeric gene can have dsRNA regions targeting 2, 3, 4, 5, 6, 7, 8, 9, 10, 11, 12, 13, 14, 15, 16, 17, 18, 19, 20 or more genes from H. halys, an additional pest species, or a combination thereof. In some embodiments, a dsRNA chimeric gene of the present invention can contain several dsRNA regions which target different portions of the same gene, or target different alleles of the same gene. Also, it is convenient to include in the transforming DNA of the invention also a selectable or scorable marker gene, such as the bar, epsps or the neo gene, so that transformed plants can easily be selected by application of glufosinate, glyphosate or kanamycin, respectively, as is well known in the art. Advantageously, the plants or seeds of the invention also comprise a glufosinate or glyphosate tolerance gene besides the dsRNA chimeric gene of the invention, so that plants can be selected using application of the relevant herbicide (glufosinate or glyphosate).

Although plant delivery of a dsRNA is an embodiment of this invention, in accordance with this invention, application of the dsRNA of the invention can be done in several ways, and need not be by way of a plant expressing a dsRNA. Any method of delivery of dsRNA not contained in a plant cell is included herein, e.g., in vitro or in vivo produced dsRNA applied to an insect diet or feed, or microbially- or yeast-expressed dsRNA. dsRNA can be applied on plants on which H. halys feeds by spraying a solution of microbial/yeast spores/cells comprising the dsRNA of the invention. dsRNA species of the present invention can be applied on plants by spraying a culture, culture extract, culture supernatant, or a combination thereof, where the sprayed material comprises a microbe-expressed dsRNA. Thus, the present invention includes microbes comprising genetic elements allowing for the expression of any of the dsRNA species described herein.

In particular embodiments, the present invention provides a composition having an inhibitory nucleic acid specific for an mRNA or fragment thereof represented by one or more of SEQ ID NOs: 56, 66, and 68 or a fragment or homologue thereof. Typically, dsRNAs of the present invention are provided to a target insect pest in an amount sufficient to inhibit production of the polypeptide encoded by one or more of the full-length genes targeted by SEQ ID NOs: 56, 66, and 68 or homologues and alleles thereof. For example when H. halys is feeding on a plant or cell expressing, or containing, or coated with an inhibitory nucleic acid, the insect ingests a sufficient level of dsRNA of SEQ ID NOs: 56, 66, and 68 to result in a phenotypic effect. In addition to an inhibitory nucleic acid, an insecticidal composition of the present invention can contain one or more phagostimulants, pesticides, fungicides, or combinations thereof. The composition can be formulated to be coated to be coated on a plant, plant part, or seed. In certain aspects the inhibitory nucleic acid is combined with one or more excipients, buffering agents, carriers, etc. excipients, buffering agents, and carriers are well known in the art.

Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches.

The coating can be formulated as a spray or dip so that the inhibitory nucleic acids remain on the plant material and remain able to inhibit target protein expression in *H. halys* as the plant matures and develops. For example, the seed of a plant can be coated with a composition comprising an amount of one or more of the disclosed inhibitory nucleic acids effective to inhibit or reduce nematode disease in the plant in combination with an excipient.

dsRNA-Containing Plant Structures ("dsRNA Traps")

Described herein are novel compositions containing dsRNA(s) and methods of using them that target one or more chosen pest insects. The invention takes advantage of the vascular and/or osmotic flow of materials through living plant tissue to distribute a non-naturally-occurring dsRNA species throughout an intact and living plant material (e.g., a fruit, vegetable, leaf, stem, etc.) on which a target insect can feed. In some embodiments, the living plant material is at least partially soaked in an aqueous solution containing the one or more dsRNA species to be loaded into it for a sufficient time to allow for uptake of the dsRNA(s). Such a procedure can involve removal of a portion of the living plant material to provide access to the vascular structures. The mechanism(s) by which the living plant material takes up and distributes the dsRNA throughout its tissues is not relevant, as long as the plant material can perform these actions.

In preferred embodiments, the plant material is an attractive food source for the one or more insect pests targeted. Thus, in practicing the present invention, a variety of structures from various plants can be utilized including, but not limited to, leaves, fruits, stems and vegetables. In preferred embodiments, the plant material is capable of being fed upon by a target pest insect. By way of example only, and not intended to limit the specific sources of plant materials, certain embodiments of the present invention can include dsRNA(s) taken up and distributed through vegetables (e.g., cucumbers, green beans, snow peas, sugar snap peas, etc.), fruits (e.g., strawberries, apples, cherries, etc.), stems (e.g., tomato, cantaloupe, etc.), leaves (e.g., collard greens, spinach, kale, lettuce, etc.). One of skill in the art will recognize that the particular plant structure to serve as a source of dsRNA ingestion by a target insect pest can be chosen on the basis of multiple factors, such as the ability of the plant material to uptake the dsRNA(s), the ability of the target insect pest(s) to feed on the plant structure and the attractiveness of the plant material to the target insect pest(s).

By varying the concentration of dsRNA in the solution in which plant material is soaked, various concentrations throughout the plant structure can be achieved. Additionally, the plant material can be trimmed to desired lengths to achieve a known concentration over a given length. Thus, in some embodiments of the invention, a particular concentration can be achieved per unit length of the plant material. Such concentrations include concentrations anywhere from 0.01 µg/inch to 10 µg/inch, for example 0.01 µg/inch, 0.02 µg/inch 0.03 µg/inch, 0.04 µg/inch, 0.05 µg/inch, 0.06 µg/inch, 0.07 µg/inch, 0.08 µg/inch, 0.09 µg/inch, 0.1 µg/inch, 0.2 µg/inch, 0.3 µg/inch, 0.4 µg/inch, 0.5 µg/inch, 0.6 µg/inch, 0.7 µg/inch, 0.8 µg/inch, 0.9 µg/inch, 1.0 µg/inch, 1.1 µg/inch, 1.2 µg/inch, 1.3 µg/inch, 1.4 µg/inch, 1.5 µg/inch, 1.6 µg/inch, 1.7 µg/inch, 1.8 µg/inch, 1.9 µg/inch, 2.0 µg/inch, 2.1 µg/inch, 2.2 µg/inch, 2.3 µg/inch, 2.4 µg/inch, 2.5 µg/inch, 2.6 µg/inch, 2.7 µg/inch, 2.8 µg/inch, 2.9 µg/inch, 3.0 µg/inch, 3.1 µg/inch, 3.2 µg/inch, 3.3 µg/inch, 3.4 µg/inch, 3.5 µg/inch, 3.6 µg/inch, 3.7 µg/inch, 3.8 µg/inch, 3.9 µg/inch, 4.0 µg/inch, 4.1 µg/inch, 4.2 µg/inch, 4.3 µg/inch, 4.4 µg/inch, 4.5 µg/inch, 4.6 µg/inch, 4.7 µg/inch, 4.8 µg/inch, 4.9 µg/inch, 5.0 µg/inch, 5.1 µg/inch, 5.2 µg/inch, 5.3 µg/inch, 5.4 µg/inch, 5.5 µg/inch, 5.6 µg/inch, 5.7 µg/inch, 5.8 µg/inch, 5.9 µg/inch, 6.0 µg/inch, 6.1 µg/inch, 6.2 µg/inch, 6.3 µg/inch, 6.4 µg/inch, 6.5 µg/inch, 6.6 µg/inch, 6.7 µg/inch, 6.8 µg/inch, 6.9 µg/inch, 7.0 µg/inch, 7.1 µg/inch, 7.2 µg/inch, 7.3 µg/inch, 7.4 µg/inch, 7.5 µg/inch, 7.6 µg/inch, 7.7 µg/inch, 7.8 µg/inch, 7.9 µg/inch, 8.0 µg/inch, 8.1 µg/inch, 8.2 µg/inch, 8.3 µg/inch, 8.4 µg/inch, 8.5 µg/inch, 8.6 µg/inch, 8.7 µg/inch, 8.8 µg/inch, 8.9 µg/inch, 9.0 µg/inch, 9.1 µg/inch, 9.2 µg/inch, 9.3 µg/inch, 9.4 µg/inch, 9.5 µg/inch, 9.6 µg/inch, 9.7 µg/inch, 9.8 µg/inch, 9.9 µg/inch, 10.0 µg/inch, or more. One of skill in the art will recognize that, although these values are provided in µg/inch values, any concentrations within these ranges expressed in other concentration per unit length are contemplated herein. The ranges provided also encompass all incremental concentrations between the specifically stated points.

It has been shown that providing aqueous solutions of dsRNA to plants, allows for the direct uptake of dsRNA by roots and leaves and results in transport throughout the plant (Hunter et al., (2012), supra; Bolognesi et al., PLoS One (2012) 7:e47534; Molnar et al., Genome Biol., (2011) 12:215). Thus, solutions of dsRNAs provided herein can be applied directly to plants, allowing for uptake by the treated plants. In most instances, the dsRNA is transported throughout the plant via the vascular system (or cell transport in non-vascular plants) after uptake through foliage or roots. Organisms that then feed upon, colonize, infect, or otherwise come into contact with the dsRNA incorporated into the treated plants (such as by ingesting sap, or invading plant tissues) are then exposed to the dsRNA via ingestion or uptake.

Aqueous dsRNA compositions of the invention disclosed herein can be applied to soil, fruits, vegetables, crops, and any other desired target using any delivery methodology known to those of skill in the art. For example, the compositions can be applied to the desired locale via methods and forms including, but not limited to, shank injection, sprays, granules, flood/furrow methods, sprinklers, fumigation, root soaking and drip irrigation. In embodiments of the invention where the compositions are sprayed onto a desired locale, the compositions can be delivered as a liquid suspension, emulsion, microemulsion or powder. In other embodiments, granules or microcapsules can be used to deliver the compositions of the invention.

The compositions of the present invention can be applied to plants and/or crops by any convenient method, for example, by using a fixed application system such as a center pivot irrigation system. Preferably, application to fields of plants and/or crops is made by air spraying, i.e., from an airplane or helicopter, or by land spraying. For example, land spraying may be carried out by using a high flotation applicator equipped with a boom, by a back-pack sprayer or by nurse trucks or tanks. One of skill in the art will recognize that these application methodologies are provided for example and that any applicable methods known in the art or developed in the future can be utilized.

In preferred embodiments, the present invention provides a composition having at least one inhibitory nucleic acid specific for an mRNA, fragment thereof, or homologue thereof present in a target insect pest. Typically, dsRNA(s) of the present invention are provided to a target insect pest in an amount sufficient to inhibit production of the targeted polypeptide encoded by one or more of the full-length genes targeted by selected dsRNA(s) or homologues and alleles thereof. For example when a target insect is feeding on dsRNA-laden plant material (e.g., leaf, root, vegetable or fruit) containing an inhibitory nucleic acid, the insect ingests a sufficient level of dsRNA to result in a phenotypic effect. In particular embodiments, a combination of two or more dsRNAs are combined in a single plant material. In embodiments where two or more dsRNAs are combined in a single plant material the dsRNAs can target different genes or different portions of the same gene from the same or different pest targets. Thus, in one embodiment, a single plant material can be used to deliver multiple, different dsRNA species targeting the production of one or more proteins from one or more pests. Where two or more dsRNAs are taken up and distributed throughout the vascular tissue by a plant material, the dsRNAs can be provided to the plant material in a single solution, or in multiple, sequentially-applied solutions.

In addition to an inhibitory nucleic acid, a dsRNA-containing plant material of the present invention can also comprise one or more chemoattractants, phagostimulants, visual attractants, insecticides, pheromones, fungicides, or combinations thereof. Such additional components are well known in the art and are readily chosen to complement compositions of the present invention, but are not specifically integral to the present invention. These additional components can be formulated to be coated on a plant, plant part, leaf, fruit, vegetable, stem or other plant structure. In certain aspects the additional component(s) are combined with one or more excipients, buffering agents, carriers, etc. Excipients, buffering agents, and carriers are also well known in the art.

Where additional components are applied in a coating, the coating can be formulated as a spray or dip so that the additional non-dsRNA components acids remain on the exterior of the plant material. For example, a leaf having a dsRNA distributed through at least part of its vascular system can be coated with a composition comprising one or more chemoattractants, phagostimulants, visual attractants, insecticides, pheromones, fungicides, or combinations thereof. Alternately, the additional component can be mixed with an aqueous solution containing the dsRNA(s) to be taken up and distributed via vascular action of the plant material, or osmosis through the plant material, thus distributing the dsRNA(s) and the additional component(s) throughout at least part of the plant material.

Having described the invention in general, below are examples illustrating the generation and efficacy of the invention. Neither the examples, nor the general description above should be construed as limiting the scope of the invention.

EXAMPLES

Example 1

BMSB Rearing and dsRNA Feeding Assay

Figure 1B:
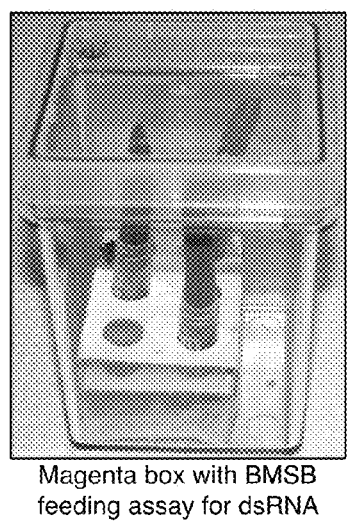

To test the per os delivery of dsRNA for RNAi in the invasive insect pest BMSB, we developed a vegetable-mediated delivery method. Lean organic green beans; *Phaseolus vulgaris* were selected as the vehicle for delivery to the animal, BMSB feeds on this cultivar crop by piercing into the vascular tissue using their needlelike stylets. Feeding occurs by alternate salivation and ingestion with slow movement of stylets in a lacerate-and-flush feeding method causing considerable damage to the cultivar crops (Peiffer & Felton 2014). This feeding technique was tested for delivery of green food color and water. A solution of green food color was mixed at 1:10 ratio with water to imitate dsRNA. Slender green beans were trimmed from the calyx end for a total length of 3 inches. These beans were inverted and immersed into either the food color solution or water in a 2 ml microcentrifuge tube. Due to absorption or capillary action the solution was absorbed into the phloem and circulated reaching the style of the bean through the vascular tissue. This was indicated by the green coloration of the peripheral vascular tissue at the style (FIG. 1A). A total of three beans per magenta vessel to 3 animals were treated (FIG. 1B).

*H. halys* (BMSB) insects were reared at USDA-ARS in the Beltsville Agricultural Research Center, Beltsville, Md. (Khrimian, A., J. Natural Prods., (2014) 77(7):1708-17). This colony was established in 2007 from adults collected in Allentown, Pa., and supplemented with several animals collected at Beltsville, Md. Insects were reared in ventilated plastic cylinders (21621 cm OD) on a diet of organic green beans, shelled sunflower and buckwheat seeds (2:1, w/w), and distilled water supplied in cotton-stopped shell vials. Eggs were collected weekly, hatched in plastic Petri dishes with a water vial. After the animals molted to second-instars, nymphs were transferred to larger rearing cages till adults. Adults, males and females were separated 1 to 2 days post emergence, and subsequently maintained in different containers. The insects were maintained in Thermo Forma chambers (Thermo Fisher Scientific) at 25° C. and 72% relative humidity, under a 16L:8D photoperiod.

Figure 1C:
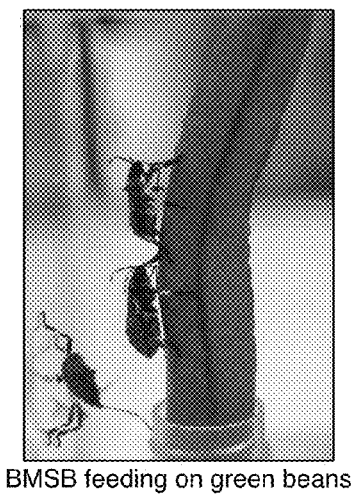
Figure 1D:
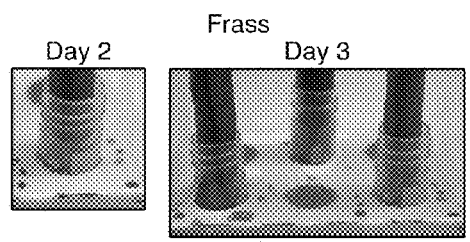

For the feeding assays early $4^{th}$ instar nymphs of BMSB were selected that were hatched preferably from the same egg mass. The animals were then starved for 24 hrs prior to resuming feeding. The animals were treated in groups of three per magenta vessel containing three green beans, or three green beans with green food color, or dsRNA as mentioned below. The animals readily fed on the upright green beans by inserting their stylets into the vascular tissues (FIG. 1C). If the animal fed on beans immersed in green food color then it could be assumed the resulting green frass was indicative of treatment delivered orally and passed through the gut before being excreted. Green frass was observed on day 2 of feeding visualized as green dots, which further increased in content on the day three (FIG. 1D). Further results confirmed that dsRNA could also be fed to these insects in this manner (see below).

Green beans were washed with 0.2% sodium hypochlorite solution (J.T. Baker) for five minutes followed by three washes with ddH$_2$O. The beans were trimmed from the calyx end to a total length of 3 inches. Next the beans were immersed in a cap-less 2 ml microcentrifuge tube containing 300 ml solution of 1:10 dilution of green food coloring or dsRNA in RNase DNase free water. Lean green beans were selected for this diet to ensure the beans fit in the 2 ml microcentrifuge tubes (1 cm). To prevent any evaporation of the solution or dust or insects entering the solution, the microcentrifuge tubes containing the beans were sealed with parafilm. These tubes were kept at room temperature for 3 hours allowing for the solution to rise to the style of the green bean through capillary action. The tubes were further placed in a small box to keep them upright and enclosed in magenta jars (Sigma) (FIG. 1B). The BMSB nymphs were allowed to feed on these beans for a period of 5 days. The diets were refreshed with dsRNA and beans on the third day of feeding.

Example 2

Analysis of Specific BMSB Genes Utilizing In Vitro Synthesized dsRNA

Genes specific to BMSB were selected by examining the transcriptome of BMSB (Sparks et al., PLoS One, (2014) 39(1):e111646), and regions of interest for each gene selected that varied between 200 to 500 base pairs (Table 1).

TABLE 1

Potential *H. halys* target genes and predicted dsRNA size

| Gene Name/Homology | Size | Abbreviation |
| --- | --- | --- |
| Vitellogenin-A1-like | 491 | Vitellogenin |
| BTB/POZ domain-containing protein 17 | 374 | BTB/POZ |
| Hypothetical protein comp 37491 | 348 | HP c37491 |
| Adenosylhomocysteinase 3-like (1) | 404 | AHCY (1) |
| Adenosylhomocysteinase 3-like (2) | 506 | AHCY (2) |
| Adenosylhomocysteinase 3-like (3) | 524 | AHCY (3) |
| ftz transcription factor 1 | 468 | FTZ |
| Probable cytochrome P450 49a1-like (1) | 442 | Cytochrome P450 (1) |
| Probable cytochrome P450 49a1-like (2) | 539 | Cytochrome P450 (2) |
| Arginine kinase | 465 | Arginine Kinase or AK |
| Dopachrome conversion enzyme | 498 | Dopachrome |
| Farnesyl pyrophosphate synthase-like | 512 (observed 300) | FPPS1 |
| Juvenile hormone acid O-methyltransferase-like | 545 (observed 700) | Juvenile Hormone or JH |

PCR products were then generated by polymerase chain reaction (PCR) by amplifying genomic DNA using specific oligonucleotides (Table 2) and purified using a PCR purification kit (Qiagen). This PCR amplified region was then used as template to generate dsRNA required for RNAi in BMSB. The primers used for PCR contained the T7 promoter sequence. LacZ, a gene that encodes β-galactosidase was amplified from the *E. coli* genomic DNA and served as a negative control (mock) for RNAi (Table 3). The PCR-amplified DNA was purified using a PCR purification kit (Qiagen). In vitro transcription to yield dsRNA was performed by combining 250 mM HEPES pHH 7.5, 32 mM magnesium chloride, 10 mM Dithiothreitol (DTT), 2 mM spermidine, 25 mM each of rNTPs, 0.25 units of SUPERase In RNase inhibitor (Life Technologies), and 0.5 µg PCR amplified DNA in a final volume of 20 µl were incubated at 37° C. for 5 min. After 5 min, 1 µg T7 RNA polymerase was added to the reaction and further incubated at 37° C. overnight.

Figure 2:
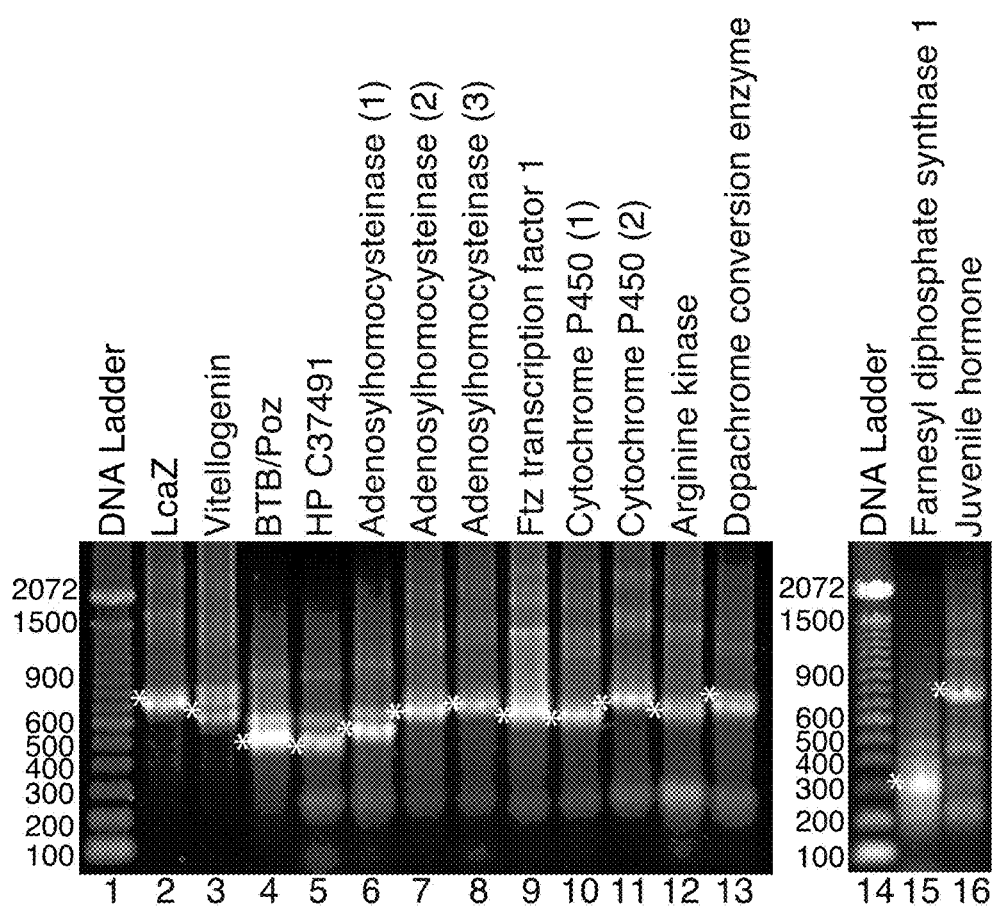
FIG. 2 provides a pictorial representation of in vitro transcription of dsRNA. PCR products of LacZ (lane 2), Vitellogenin (lane 3), BTB/Poz (lane 4), HP C37491 (lane 5), Adenosylhomocysteinase (1) (lane 6), Adenosylhomocysteinase (2) (lane 7), Adenosylhomocysteinase (3) (lane 8), Ftz transcription factor 1 (lane 9), Cytochrome P45 (1) (lane 10), Cytochrome P45 (2) (lane 11), Arginine kinase (lane 12), Dopachrome conversion enzyme (lane 13), Farnesyl diphosphate synthase 1 (lane 15), Juvenile hormone (lane 16) flanked with converging T7 promoter sequence on each side was in vitro transcribed using T7 polymerase. The resulting dsRNA denoted by an asterisk (*) was in vitro transcribed followed by electrophoresis on 1% agarose and visualized by staining with Sybr Gold (Life Technologies) alongside a DNA ladder (Lanes 1 and 14).
Figure 3A:
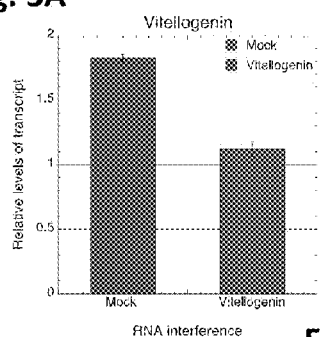
FIGS. 3A-3K provide a quantitative RT-PCR analysis of transcript levels after RNAi mediated depletion of genes fed (5 μg dsRNA diet). Total RNA from the entire BMSB nymph fed on 5 μg dsRNA using a green bean mediated delivery system consisting of gene targets; Vitellogenin (FIG. 3A), BTB/Poz (FIG. 3B), HP C37491 (FIG. 3C), Adenosylhomocysteinase (1) (FIG. FIG.), Adenosylhomocysteinase (2) (FIG. 3E), Adenosylhomocysteinase (3) (FIG. 3F), Ftz transcription factor 1 (FIG. 3G), Cytochrome P45 (1) (FIG. 3H), Cytochrome P45 (2) (FIG. 3I), Arginine kinase (FIG. 3J) and Dopachrome conversion enzyme (FIG. 3K) was isolated and the levels of transcripts were measured by qPCR. LacZ RNAi (Mock) served as control. 18s RNA was used as an internal standard to correct for differences in RNA recovery from tissues. Results are from three biological replicates, and error bars indicate ±SEM.
Figure 3B:
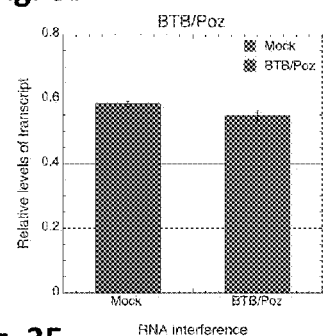
Figure 3C:
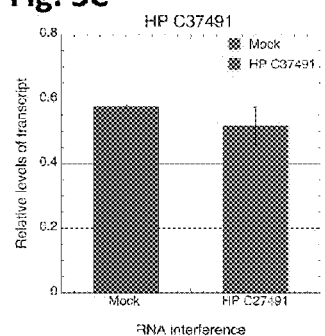
Figure 3D:
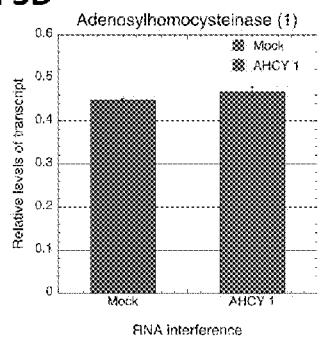
Figure 3E:
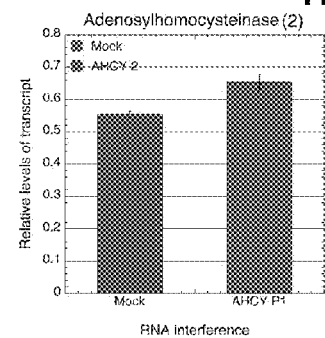
Figure 3F:
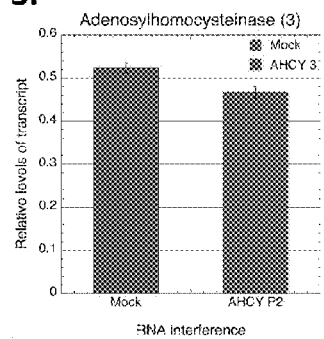
Figure 3G:
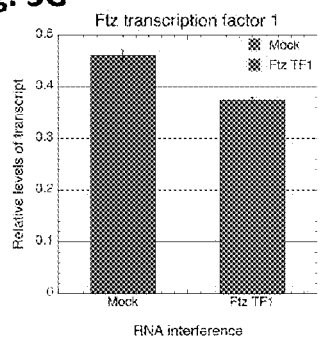
Figure 3H:
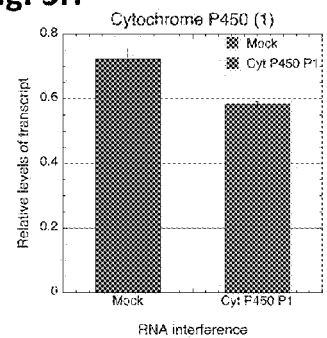
Figure 3I:
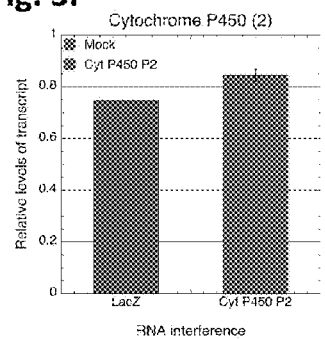
Figure 3J:
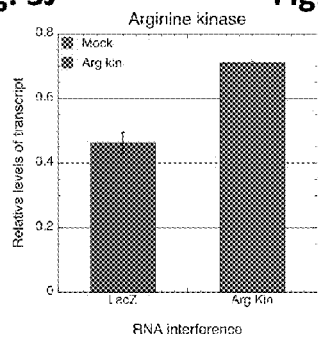
Figure 3K:
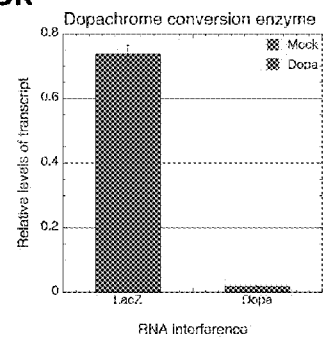

The reactions were then centrifuged for 2 min at 13,000 rpm to pellet the magnesium pyrophosphate. The supernatant was transferred was treated with 2 units of RQ1 DNase followed by incubation at 37° C. for 30 min. The reaction mixture was extracted with an equal volume of phenol/chloroform/isoamyl alcohol (25:24:1) and centrifuged. The aqueous layer was extracted with chloroform. One-fifth-volume ammonium acetate (5 M ammonium acetate+100 mM EDTA) and 3 volumes of chilled 100% ethanol were added to the resulting aqueous layer. After incubating on ice for 10 min, the dsRNA was precipitated, washed with 75% ethanol, resuspended in nuclease free water and stored in the freezer for use. To test the quality and size, dsRNA was analyzed on a 1% agarose gel and visualized by staining with SYBR GOLD (Life technologies) (FIG. 2). The exogenously transcribed dsRNA (FIG. 2, lanes 3-13) was evaluated alongside a DNA marker (FIG. 2, lane 1). LacZ dsRNA was also synthesized and used as a control (FIG. 2, lane 2). The dsRNA visualized seemed to be of high quality and stable.

TABLE 2

PCR Primers.

| Gene | Direction | Sequence (5'-3') |
| --- | --- | --- |
| Vitellogenin | Forward | CAATTTGATCCACCGACTGTT (SEQ ID NO: 1) |
| Vitellogenin | Reverse | CCGCATGAATCTTACTCTGGA (SEQ ID NO: 2) |
| BTB/Poz | Forward | TGCAATATTGGAAATAAAGAAGTCA (SEQ ID NO: 3) |
| BTB/Poz | Reverse | TTTGTAACACCATGTGCCAAT (SEQ ID NO: 4) |
| HP c37491 | Forward | AAACATCATTGCTCATTTAATCTCTT (SEQ ID NO: 5) |
| HP c37491 | Reverse | AAATTTGGACCTGTGTAGGG (SEQ ID NO: 6) |
| AHCY (1) | Forward | AATGTTTCGCAAGGCTATTG (SEQ ID NO: 7) |
| AHCY (1) | Reverse | GTCCTAACCCTGTCGTCCTT (SEQ ID NO: 8) |
| AHCY (2) | Forward | TCACAGCAGAAACAAACCAA (SEQ ID NO: 9) |
| AHCY (2) | Reverse | ACTGTGGGCACATATGACG (SEQ ID NO: 10) |
| AHCY (3) | Forward | CAGTGCCTAACTTGTTTCAGTG (SEQ ID NO: 11) |
| AHCY (3) | Reverse | GGTCTTTTGATGTGTTTCTGAAG (SEQ ID NO: 12) |
| Ftz TF1 | Forward | ATGCTTGTGTGCAAGGTGTT (SEQ ID NO: 13) |
| Ftz TF1 | Reverse | TTTCCCTGAAGGTTGTTGAAA (SEQ ID NO: 14) |

TABLE 2-continued

PCR Primers.

| Gene | Direction | Sequence (5'-3') |
|---|---|---|
| Cytochrome P450 (1) | Forward | TGACTTCATATGCCCCTGTTT (SEQ ID NO: 15) |
| Cytochrome P450 (1) | Reverse | TTGCAACAAAGAAAGTGCAAA (SEQ ID NO: 16) |
| Cytochrome P450 (2) | Forward | TGCCATGACAAATGTTACCC (SEQ ID NO: 17) |
| Cytochrome P450 (2) | Reverse | TGGTATCGGTACTTTCAATCCA (SEQ ID NO: 18) |
| Arginine Kinase | Forward | AAAGGAACTTTAACTGCCATTTG (SEQ ID NO: 19) |
| Arginine Kinase | Reverse | TCATTGCAAATATGTTGCTGTAT (SEQ ID NO: 20) |
| Dopachrome | Forward | ATGATGGCATATTCGGCATT (SEQ ID NO: 21) |
| Dopachrome | Reverse | AATCGTCACAAGGCGTACCT (SEQ ID NO: 22) |
| FPPS1 | Forward | GGCAATTCAGGGATAGGACA (SEQ ID NO: 23) |
| FPPS1 | Reverse | GCATCACGTACTCTGGCATC (SEQ ID NO: 24) |
| Juvenile hormone | Forward | GGATGCTTATGAATAATCCAG (SEQ ID NO: 25) |
| Juvenile hormone | Reverse | GTATAGGATTGCCATTTTGG (SEQ ID NO: 26) |

TABLE 3

T7 PCR Primers

| Gene | Direction | Sequence (5'-3') |
|---|---|---|
| Vitellogenin | Forward | GAATTAATACGACTCACTATAGGGAGACCAAAGTTGGAAGGGAATGA (SEQ ID NO: 27) |
| Vitellogenin | Reverse | GAATTAATACGACTCACTATAGGGAGACCGCATGAATCTTACTCTGGA (SEQ ID NO: 28) |
| BTB/Poz | Forward | GAATTAATACGACTCACTATAGGGAGATGCAATATTGGAAATAAAGAAGTCA (SEQ ID NO: 29) |
| BTB/Poz | Reverse | GAATTAATACGACTCACTATAGGGAGATTTGTAACACCATGTGCCAAT (SEQ ID NO: 30) |
| HP c37491 | Forward | GAATTAATACGACTCACTATAGGGAGAAAACATCATTGCTCATTTAATCTCTT (SEQ ID NO: 31) |
| HP c37491 | Reverse | GAATTAATACGACTCACTATAGGGAGAAAATTTGGACCTGTGTAGGG (SEQ ID NO: 32) |
| AHCY (1) | Forward | GAATTAATACGACTCACTATAGGGAGAAATGTTTCGCAAGGCTATTG (SEQ ID NO: 33) |
| AHCY (1) | Reverse | GAATTAATACGACTCACTATAGGGAGAGTCCTAACCCTGTCGTCCTT (SEQ ID NO: 34) |
| AHCY (2) | Forward | GAATTAATACGACTCACTATAGGGAGATCACAGCAGAAACAAACCAA (SEQ ID NO: 35) |
| AHCY (2) | Reverse | GAATTAATACGACTCACTATAGGGAGAACTGTGGGCACATATGACG (SEQ ID NO: 36) |
| AHCY (3) | Forward | GAATTAATACGACTCACTATAGGGAGACAGTGCCTAACTTGTTTCAGTG (SEQ ID NO: 37) |
| AHCY (3) | Reverse | GAATTAATACGACTCACTATAGGGAGAGGTCTTTTGA |

TABLE 3-continued

T7 PCR Primers

| Gene | Direction | Sequence (5'-3') |
|---|---|---|
| | | TGTGTTTCTGAAG (SEQ ID NO: 38) |
| Ftz TF1 | Forward | GAATTAATACGACTCACTATAGGGAGAATGCTTGTGT GCAAGGTGTT (SEQ ID NO: 39) |
| Ftz TF1 | Reverse | GAATTAATACGACTCACTATAGGGAGATTTCCCTGAA GGTTGTTGAAA (SEQ ID NO: 40) |
| Cytochrome P450 (1) | Forward | GAATTAATACGACTCACTATAGGGAGATGACTTCATA TGCCCCTGTTT (SEQ ID NO: 41) |
| Cytochrome P450 (1) | Reverse | GAATTAATACGACTCACTATAGGGAGATTGCAACAAA GAAAGTGCAAA (SEQ ID NO: 42) |
| Cytochrome P450 (2) | Forward | GAATTAATACGACTCACTATAGGGAGATGCCATGACA AATGTTACCC (SEQ ID NO: 43) |
| Cytochrome P450 (2) | Reverse | GAATTAATACGACTCACTATAGGGAGATGGTATCGGT ACTTTCAATCCA (SEQ ID NO: 44) |
| Arginine Kinase | Forward | GAATTAATACGACTCACTATAGGGAGAAAAGGAACTT TAACTGCCATTTG (SEQ ID NO: 45) |
| Arginine Kinase | Reverse | GAATTAATACGACTCACTATAGGGAGATCATTGCAAA TATGTTGCTGTAT (SEQ ID NO: 46) |
| Dopachrome | Forward | GAATTAATACGACTCACTATAGGGAGAATGATGGCAT ATTCGGCATT (SEQ ID NO: 47) |
| Dopachrome | Reverse | GAATTAATACGACTCACTATAGGGAGAAATCGTCACA AGGCGTACCT (SEQ ID NO: 48) |
| FPPS 1 | Forward | GAATTAATACGACTCACTATAGGGAGAGGCAATTCAG GGATAGGACA (SEQ ID NO: 49) |
| FPPS 1 | Reverse | GAATTAATACGACTCACTATAGGGAGAGCATCACGTA CTCTGGCATC (SEQ ID NO: 50) |
| Juvenile hormone | Forward | GAATTAATACGACTCACTATAGGGAGAGGATGCTTAT GAATAATCCAG (SEQ ID NO: 51) |
| Juvenile hormone | Reverse | GAATTAATACGACTCACTATAGGGAGAGTATAGGATT GCCATTTTGG (SEQ ID NO: 52) |
| LacZ | Forward | GAATTAATACGACTCACTATAGGGAGATGAAAGCT GGCTACAGGA (SEQ ID NO: 53) |
| LacZ | Reverse | GAATTAATACGACTCACTATAGGGAGAGCAGGCTT CTGCTTCAAT (SEQ ID NO: 54) |

Example 2

Total RNA Isolation from BMSB and qPCR Analysis

Expression levels of transcripts were measured by quantitative realtime PCR (qPCR) using SYBR green PCR master mix SensiMix SYBR from Bioline. qPCR reactions were performed on an Applied Biosystems 7500 real-time PCR system, ABI. Data were analyzed with ABI Prism sequence detection system software. All analysis was performed in the linear range of qPCR amplification. Standards were determined by serial dilution of the cDNA prepared from total RNA isolated from gut tissue of a normal animal and used as a reference standard for the quantification of cDNA produced from RNA. 18s RNA was used as an internal standard to correct for differences in RNA recovery from tissues (Sparks et al, supra). The data was plotted using KALEIDAGRAPH (Synergy software). Primers used for qPCR analysis are as listed in Table 5.

Figure 4A:
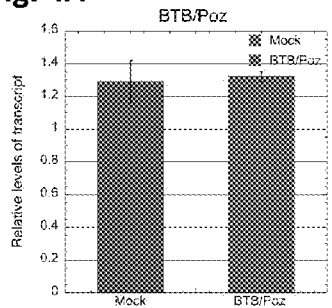
FIGS. 4A-4I provide a quantitative RT-PCR analysis of transcript levels after RNAi mediated depletion of genes fed (20 μg dsRNA diet). Total RNA from the entire BMSB nymph fed on 5 μg dsRNA using a green bean mediated delivery system consisting of gene targets; BTB/Poz (FIG. 4A), HP C37491 (FIG. 4B), Adenosylhomocysteinase (1) (FIG. 4C), Adenosylhomocysteinase (2) (FIG. 4D), Adenosylhomocysteinase (3) (FIG. 4E), Ftz transcription factor 1 (FIG. 4F), Cytochrome P45 (1) (FIG. 4G), Cytochrome P45 (2) (FIG. 4H) and Arginine kinase (FIG. 4I) was isolated and the levels of transcripts were measured by qPCR. LacZ RNAi (Mock) served as control. 18s RNA was used as an internal standard to correct for differences in RNA recovery from tissues. Results are from three biological replicates, and error bars indicate ±SEM.
Figure 4B:
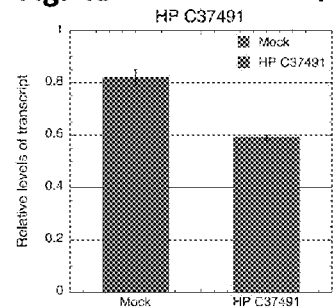
Figure 4C:
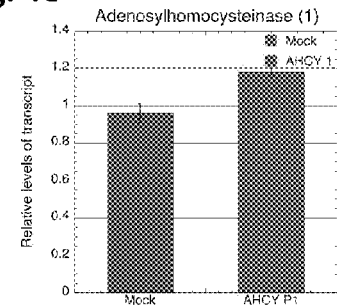
Figure 4D:
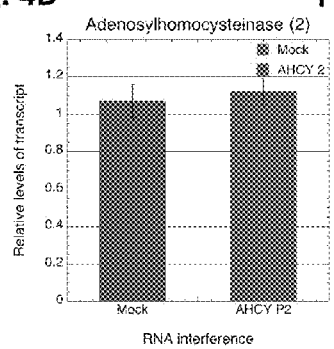
Figure 4E:
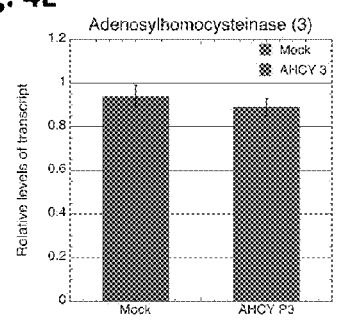
Figure 4F:
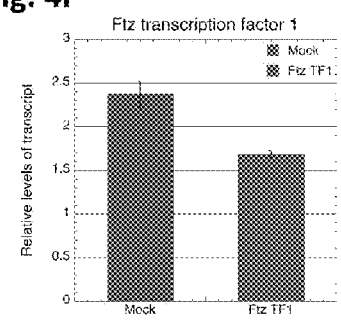
Figure 4G:
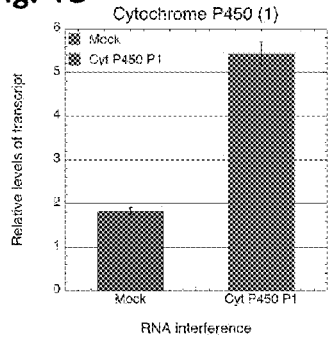
Figure 4H:
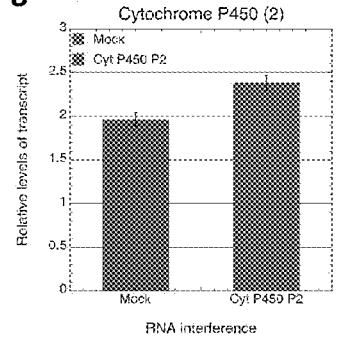
Figure 4I:
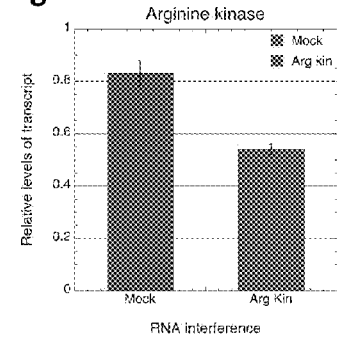
Figure 5A:
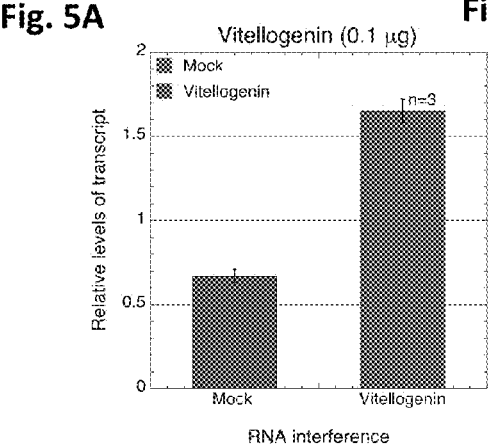
FIGS. 5A-5E provide an analysis of RNAi-mediated depletion of vitellogenin in a concentration dependent manner. Total RNA from the entire BMSB nymphs fed on green bean mediated Vg dsRNA of concentrations 0.1 μg (FIG. 5A); 1 μg (FIG. 5B), 5 μg (FIG. 5C), 10 μg (FIG. 5D) and 20 μg (FIG. 5E) was isolated and the levels of transcripts were measured by qPCR. LacZ RNAi (Mock) served as control. 18s RNA was used as an internal standard to correct for differences in RNA recovery from tissues. Results are from three biological replicates unless otherwise indicated, and error bars indicate ±SEM or variation.
Figure 5B:
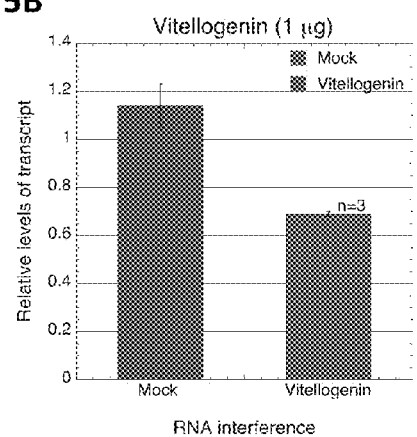
Figure 5C:
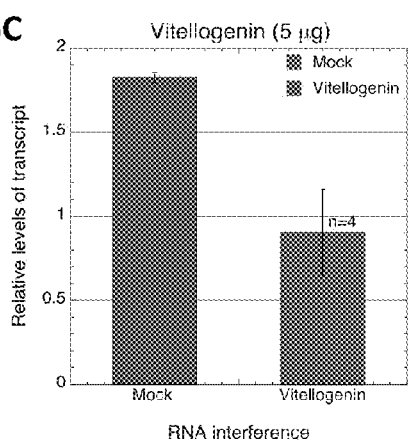
Figure 5D:
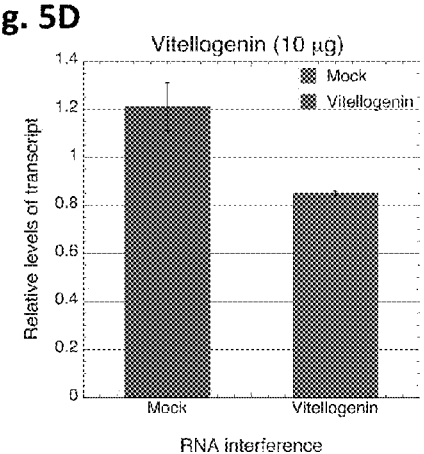
Figure 5E:
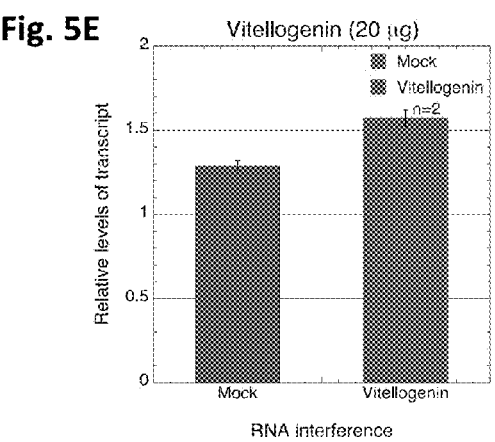

To measure the level of gene expression in BMSB, the entire animal was homogenized in 1 ml TRIzol (Invitrogen) using a micro-pestle subsequent to dsRNA treatment and total RNA was isolated from this homogenized tissue samples as per protocol. Reverse transcriptase PCR was used to generate cDNA; 200 ng of total RNA was incubated with a 0.5 mM deoxynucleoside triphosphate mixture, 0.65 μM each oligo(dT)$_{16}$ (Life Technologies), and random hexamers (Life Technologies) at 65° C. for 5 min. A cDNA synthesis mixture containing 10 mM dithiothreitol (DTT), 100 units of Superscript Reverse Transcriptase III (Life Technologies), and 2 units of SUPERase In RNase inhibitor (Life Technologies) was then added to the total RNA mixture, which was incubated at 25° C. for 5 min, 50° C. for 50 min. The reaction was terminated by incubation at 70° C. for 15 min. The resulting cDNA was then evaluated with gene specific primers listed in Table 5 by qPCR.

dsRNA-mediated depletion of the aforementioned genes was tested in BMSB through oral feeding as described above. BMSB 4$^{th}$ instar nymphs were fed on green beans immersed in 5 μg of respective dsRNAs for 5 days and transcript levels of target genes were analyzed (FIGS. 3A-3K). The corresponding qRT-PCR expression analysis showed that only vitellogenin, and dopachrome displayed significant depletion (FIGS. 3A and 3K), while BTB/Poz, AHCY (3), Ftz and Cytochrome P450 exhibited minimal gene knockdown (FIGS. 3B, 3F, 3G and 3H). Genes that displayed low levels of depletion at 5 μg, were further tested by increasing the concentration of dsRNA in the diet to 20 μg (FIGS. 4A-4I). This increased concentration of ingested dsRNA further diminished the levels of in vivo-expressed transcripts for HP C37491, Ftz F1 and AK (FIGS. 4B, 4F and 4I). However genes that displayed no depletion in the 5 μg diet experiment also showed no depletion in the 20 μg diet assay. These results demonstrate two important factors. First, that the green-bean feeding route successfully delivers dsRNA to the insects. Second, that the dsRNA species were not all capable of inducing reduction in transcript levels after ingestion.

TABLE 4 dsRNA species for RNAi analysis

| Source | Sense Strand Sequence |
|---|---|
| LacZ | TGAAAGCTGGCTACAGGAAGGCCAGACGCGAATTATTTTTGATGGCGTTAACTCGGCG<br>TTTCATCTGTGGTGCAACGGGCGCTGGGTCGGTTACGGCCAGGACAGTCGTTTGCCGTC<br>TGAATTTGACCTGAGCGCATTTTTACGCGCCGGAGAAAACCGCCTCGCGGTGATGGTGC<br>TGCGCTGGAGTGACGGCAGTTATCTGGAAGATCAGGATATGTGGCGGATGAGCGGCAT<br>TTTCCGTGACGTCTCGTTGCTGCATAAACCGACTACACAAATCAGCGATTTCCATGTTG<br>CCACTCGCTTTAATGATGATTTCAGCCGCGCTGTACTGGAGGCTGAAGTTCAGATGTGC<br>GGCGAGTTGCGTGACTACCTACGGGTAACAGTTTCTTTATGGCAGGGTGAAACGCAGG<br>TCGCCAGCGGCACCGCGCCTTTCGGCGGTGAAATTATCGATGAGCGTGGTGGTTATGCC<br>GATCGCGTCACACTACGTCTGAACGTCGAAAACCCGAAACTGTGGAGCGCCGAAATCC<br>CGAATCTCTATCGTGCGGTGGTTGAACTGCACACCGCCGACGGCACGCTGATTGAAGC<br>AGAAGCCTGC (SEQ ID NO: 55) |
| Vitellogenin-<br>A1-like | GTTAAACTAGGTGGCTGACAAGAAAAAGACTCGCGACTAGTTCATTCTTAAGCTAGAC<br>ACCGCGGAGTAAGTAAACTCCAACACCTCCTTCTATAAGAAGCGATCTCGACTAACTAC<br>TTGAGAGTGATCTCCTACTTCTCGAACTCCTGCTTCTTCGAGGAACAGATTAACCCAAT<br>ATGGACAAAAGGAGTCTGCTTGATGATCTCGATCAACTAAGCGAACTTGACGACAACC<br>CAACTCCCCCTCCACAACGACTAGAACAAAAAGAGAAGTATGAAACTAAGGTAAATAA<br>AAGAAGTGATGACCTCCTTCTCGAACTCCTGCTTCTACTTCTTCTGCTACTTCAACTTAG<br>TCTTGGAAGCGATGATAGTGGTAAAACACCTATAGGTATAAGTATAAGCATCGGGTTT<br>AATAATTTGCGGAATCCTGATAAATACGAGTCCAGACTTGGAAACACCCCGTGATGGT<br>ATAGGTCTCATTCTAAGTACGCC (SEQ ID NO: 56) |
| BTB/POZ<br>domain-<br>containing<br>protein 17 | ACGTTATAACCTTTATTTCTTCAGTGTTATTTAGTGATTATATTGTTTAATAATGTTATCT<br>GTAACACAATATGTGTTAATCCATTGTACCGTATTTGATTTACCATCGATATTGTAACAT<br>AGTAATTTAAATATGTTATACATACATTCGTTGTTATTCAACTAAACCGATTGGCTTTAC<br>TTGTAAGTCGATGTCTCAGTAGTGTGGTAAAGAGTTGCGGAAAATATATTAATATCTAA<br>AGGATATTAAATTTTATGGACGAAAGTGAAGTCTCGTCTATAACTTGGGATAGCTAGAT<br>AATTCAGTAATTGTAAGGTAAGAAAAAGAACACCGTTTAAATGTCAAAATGTAATAAC<br>CGTGTACCACAATGTTT (SEQ ID NO: 57) |
| HP c37491 | AAACATCATTGCTCATTTAATCTCTTAAAGATTCTCTTACATATCGATTGTTTTATTGAC<br>AAATTTTAAAAAGAAAACAAAAAGATGGTAGGAATAATTTTCTATGTTGTTTGTATTTT<br>TATGACTGTTAGAAATGATGTTAAAAATTATTGTAATAAATTCATGTTCTGTCATCAGT<br>ATCTTTTTATTTTTTCATTTATGTTTATGAATATAACTATCCATTCTTTGAAACTCAGAAA<br>TCGTAATTGTAAATGAACGTATTACTTATCATGTATACTAGTATTTGGTCTCTTCATTTA<br>TTAGTTTACTGAACTTTGTTTAAATGTAACCCTACACAGGTCCAAATTT (SEQ ID NO: 58) |
| Adenosyl-<br>homocysteinase<br>3-like (1) | TTACAAAGCGTTCCGATAACAATAATAACAGTGGACTTATGGACATTGACAAAGAAAA<br>TCTTTCGAAATGTAAATTTGTTATAATATTTAAAATTTTTATCTTTTTTGGGTATCCTTTC<br>TTTTGGAATTCGGTTAGAGAACTAAACCAGTGACAATTAGTTCTACCACTCTTTTGTAA<br>CGGGATGTTAACTACGGATCATCGATATACAACGTTTTATAATTCATTGTTTTTAAATA<br>AACTCGTTTTTGACCAAGGTTCAAGGGCAATAGAATAAGTGAGTAGTGGTATGGTCTCC<br>AATCTTGTTAGTTATTTTGTAAGTAGTTCGACGCAGAGTCAGGAAAGTAGGGTGTTTA<br>CTAAAATTATTTTGATGAAATCTGACTTTTTCCTGCTGTCCCAATCCTG (SEQ ID NO: 59) |
| Adenosyl-<br>homocysteinase<br>3-like (2) | AGTGTCGTCTTTGTTTGGTTGTGTTGTAACAAAGTCGTCATACAGTTATCATTCTCCAGT<br>ATGACTCTCTATATTATACAATACTCTCACATTTGTTAAAGAAACTATAATGTCTTACAA<br>TAAGATCTCAAGATTCGTACCGTATTTTTCTATTAAATATATTAAATTTTTTCTTTTTTA<br>CATTTTTAGTTCGTTAAAGAGATCCTCTGTGGTTATGAAATTAATCGGTTGGTCATTTAG<br>AAAGGATTTAAATTTTAGAAGTACGAGATCCAGTCTCCAAAAGTTATGACACGGACGA<br>CCGTGTTAATAAGGGTGGATTATTTTGAAAATGGTTGATAGTGGTTCCTTTGAATATAC<br>ATAAGTCTCCACGATTTTTACTGTTATCATAGCTAAAACTCTACCGAACGAGCACATAG<br>CTAAATAAAATTATAAAGTCTAAAAATTATATAATCCCGTTTCCAGGGGGAGTTGTGAA<br>ACCCTCGGACTGCAGTATACACGGGTGTCA (SEQ ID NO: 60) |
| Adenosyl-<br>homocysteinase<br>3-like (3) | GTCACGGATTGAACAAAGTCACTATTGGTACCTTTGAATACAAAATCCCTGACATCTTT<br>TATTTTTACGATGGTTAAAATTCTAGCGGATAACTAACTAAAAGTTTATAACCTAAAGA<br>CTATAAAATCTCAGGGATTTATACAAAAGGTTCTATATCTTTTACTTTTATGAGAACTA<br>AAATTCTAGTTAACGAGTACATATCTAAAAAATTTTTTGAAAAACATAAAAATTGCATA<br>ATTCCTGGAAATTATAAAACAACTTCCCATACTTTTCACTTTTAAGTTTGCTAAACTTCT<br>AGCTTACAAGTGCATAGATAAATAAAATTGAAAAACCTAAAAATTGTATAATTTTAAT<br>AAACTATTCAAGGTTTTCTAATTATTAATTTTTAAGGTAGCTAAAATTCTAGAAAACTA<br>AGTTAAATATGTCATAAAAAGCAATGATGTGGAAGTTTTTGTTTAGTTATTCTTTAGAC |

TABLE 4-continued dsRNA species for RNAi analysis

| Source | Sense Strand Sequence |
|---|---|
| | GTTTCAGTTTTATTTAGTTATGTGACTTAGAAGTCTTTGTGTAGTTTTCTGG (SEQ ID NO: 61) |
| ftz transcription factor 1 | TACGAACACACGTTCCACAATACCTTAAATTCTCGTCATTCAAAAAAGACCGGTCCTTG ACCCTCTCACCTGCGATGTAAACCAGACCCTGTTCTCTCTATAGGGAGAGTAATCCATT GACACTTCTGTGTGTATGAATTATTTAAATGTAATTTAGATTAATAATTTATGTGCGAGT AGAAAGAGTGTTTATTTTGTTAAAAGGTTCGTTTTGAAAAACAAAGATATGTGCGTCTT GAACAACCGCTCTATTAGCCGTTTGTTGGCTACAAATGGCGTAACATAAAATTCGTTTA TTTCTTCGATTCTTTCTTATAAACAGGGCTGTGGTACTGGGAGCTCACAATTTTTTTTA CTTTTTTTTTTTATTTTTGTTCTTTGTTAATCATTTTCTTTCTGTTTCTTTTACACGTTACA GATTGTAATTATTGGCATTGGTTTTATACAAAGTTGTTGGAAGTCCCTTT (SEQ ID NO: 62) |
| Probable cytochrome P450 49a1-like (1) | ACTGAAGTATACGGGGACAAATCAAGATCATTAGGGACAAATAAGAAGAAAAGGAGA AATCTCGGAGTTCCCTACCCGGTAAGCACCGGCTCCCTCAATTTGACAGTTGAAACCGG CGGAGCAATAACGTCACCACGACCAAACTTAAGCCGGACCCCTTAACTGAATATAAAG CAACGTACATTACTTTTGGACTGGGGGGTGGTACCAATCATATCCAACCGATAGATGTC TATTGGGGGAGGTATACAAACTTTATGGTTATTTTTTCAGGGATTCCCTACGAAGACA ACAGACTAAAATGCTTCTTAACTTAACCGTGTGTTTTTATTTTATTTATAGTGAACTTT TCATTTTATACAGATTTAATAAAAAATTTCTAATTTAAATTAATAATATAAAACATTATT AATCATATAAAACGTAAAGAAACAACGTT (SEQ ID NO: 63) |
| Probable cytochrome P450 49a1-like (2) | ACGGTACTGTTTACAATGGGGATAGTAAAGGGTAATTTGGATCAACTTTGGTACGATCA GACTACATTCCTGTAACACTTTAGTGAGGAAAGTGTACTTTAAGTAACCAATGGCATGG TATCTTCAGCCGCTAGGTGATTCCTTCTCATGAATATAACACGTAAATGAGCAAAAGTG AAAGACTTGAAAGTTGACTGTGAGTGTGTTGACCTCTCTATCTGTTATTTTGGCAAAAT TGTTATATAGGAGTATTTTATACGGAACGGCTTGGTGTCCAACCCTTGGTGACGAAATC GACTTCATAGCTAAGGACTATCTTAACTTACTTTTTATAGTTAAAAGGTTCTCATAGTTT AATTTTCACCGTTACGAGTTACTTGATTCGGTTACTCGTTTTTTGTTTTTAGTCCGTTTGT ATATCTATAAAGACTATAGGTATTGGTTATGAACTCTGAACAAGATCGATTACTGAATT TTTTTTCTAATCACTTCTTAGTCATTTTTTATAGTCTTAATAACCTAACTTTCATGGCTAT GGT (SEQ ID NO: 64) |
| Arginine kinase (sense strand) | AAAGGAACTTTAACTGCCATTTGTTAATGAAGTTCTTTTCGATTGCTATACACAAGGCA AACACATTCGTTAAGATGCAACACCATATTTCATCCCCCTATCCTCCCTTCTCACTTTAA AACTCACGGATAACTTATTCCCTATTTAGTGTTGATAAGTTAATTCGTTTTAAAATAGTT GTATTAAAAAAAAAAAATTAAATGTTATTTATTAGAAAACCTATCGCCTCTGTATTCA TGTTAATTATATTTATTAGTTGCCGCACTAGTCATAGGTAATGTTTAAAAAAAAAAGCAG ATGGTTTACTGTTAATGTAACTAGTGTCGTCTATGTTGTACATTTTGTGACAACATGGAA TGTACAAATAAAAAAATAATTTTAATATAATTAATTATTATCATTACATAAATATATAT ATAATATATATATAAATGTGCTAAATATACAGCAACATATTTGCAATGA (SEQ ID NO: 65) |
| Dopachrome conversion enzyme (Protein yellow-like isoform) (sense strand) | ATGATGGCATATTCGGCATTACAATGTCACCCCGAGATATAACTGGCCGAAGGTATTTG TTCTTTCATCCATTATCCAGCTTCCGAGAGTTTCATATTGACACGATGATGCTTCAAAAC GAAACTTTTGCTAAAAGAGCAGACGAAATGATGAAACTATTGGGTGAGGAGAGGAGG ACGGATCGAGGACATGCTGCTGGCTCATCGATGGATAGAAATGGAGTTCTCTTCTATAA CCTAATATCCCTTTCTGCTGTAGGGTGTTGGAACTCTAGGCTGCCACATTATCCAGAGA CTCAAGGGATAGTTGAAACAAATAATATCACACTCTCCTTTCCAAATGATTTGAAAGTT GACAAGGAACCCATTCAAAGATTGTGGGTTTTGAGTAACCGATTGCACCGATATTTGTA TTCCAAGCTTGATCCTTCTGATGTGAATTTTAGGGTAATGACAATGCCTGTAGATGAAG CAGTGAAAGGTACGCCTTGTGACGATT (SEQ ID NO: 66) |
| Farnesyl pyrophosphate synthase-like (sense strand) | GGCAATTCAGGGATAGGACAAGTATTGGATATCCTGGACCATAAGAATTCAGATTTCA GTGATTATGCTAGTTGGAAGAACAAAGTTGAATACAAATCAAGGAATACAATGTGTGC TTTTCCAGTACTGGGTCTTCTACATGCAGGACTGACCTGTAACGACCTTATTCATAAAA CTATGGACATATTTGGTGATTATGGACTTATGTTTCAAGTATGGAATGATTTCATGGATT TCTATTCAGTGCAAGAGGAATCTGGTAAAGGAAATTATGATTGCAAGAACAATGTAAA AACTTGGGCAACTATAACAGCAATGACTCACTTTAATCCCGCCCAAGCTAAAGAGTTCA GGGACTGCTATGGGACCAACGATCCAGCTAAAAGATCTAGAGTACGCGAACTGTTTGA CGAGATAGATTTACCCAGGAAATACTTGGATTATTTAAGGAATATCCGTGTTACTGTTG AAAAAAAAATCGGTGAACTTAGTGATGCCAGAGTACGTGATGC (SEQ ID NO: 67) |
| Juvenile hormone acid O-methyl-transferase-like (sense strand) | GGATGCTTATGAATAATCCAGAGCTGTATACAAATGTAAATGCATTGCAAAAACGCGA TGCACAAGAGGTCTTGGAAGAAGTTAAAGATCTATTACCATGGTCTATAGGAGAAAAC GTGCTAGATGTTGGCTGTGGACCTGGTGATCTCACATCCTCCCTTCTCACTTCATATCTG GCCAATGACTATCGAGTGGTCGGTTGCGATATTTCTGAAGCTATGGTGAAATATGCTCA AGCAAATATGGAAACGATCAATTTTGTTTCAAACAGCTTGATATCAGCAATGGAAAT ATATGGATGAACTGGGAAGAGGAGATTTTTGATAAAGTATTTTCATTTTACTGCCTTCA CTGGGTTAAAGATCAGATACAAGCAGCAGAAAACATTTATAGTTTGCTGAAAGATGGT GGTTATTTTGTCACAATGTTCACTATATCTCATCCGTTTCTTATTCTATTTAGCAGACTTA AGGAAAACCCAAAATGGCAATCCTATAC (SEQ ID NO: 68) |

TABLE 5 qPCR Primers.

| Gene | Direction | Sequence (5'-3') |
|---|---|---|
| Viteilotlenin | Forward | TTGATAGTTGTTTGGATTTTGAAGGT (SEQ ID NO: 69) |
| Viteilotlenin | Reverse | TCTTACTTGATCAGCGCTCAGAA (SEQ ID NO: 70) |
| BTB/Poz | Forward | AACTACCTCGACGGGATGAT (SEQ ID NO: 71) |
| BTB/Poz | Reverse | CATATCACCATTGTGCCTTTGTC (SEQ ID NO: 72) |
| HP c37491 | Forward | TTGTTTAAATGTAACCCTACACAGG (SEQ ID NO: 73) |
| HP c37491 | Reverse | CACACAAACTGATGTAGATGAACTC (SEQ ID NO: 74) |
| AHCY (1) | Forward | AGTCCTTTCATCCCACAAA (SEQ ID NO: 75) |
| AHCY (1) | Reverse | GGATTTAAGACAGTTGTGTTCTG (SEQ ID NO: 76) |
| AHCY (2)/(3) | Forward | CATATGTGCCCACAGTGCCTAA (SEQ ID NO: 77) |
| AHCY (2)/(3) | Reverse | GGCGATCTTAAAATTGGTAGCATT (SEQ ID NO: 78) |
| Ftz TF1 | Forward | AGAAAGACAAAGAAAATGTGCAATGT (SEQ ID NO: 79) |
| Ftz TF1 | Reverse | ACATTCCAAAAACAGTTTCAACCA (SEQ ID NO: 80) |
| Cytochrome P450 (1) | Forward | CCTCATTCTACACAAGAGAACTAATCAATAG (SEQ ID NO: 81) |
| Cytochrome P450 (1) | Reverse | GCTCTAAAGAGGAAAAGAAGAATAAACAG (SEQ ID NO: 82) |
| Cytochrome P450 (2) | Forward | TTTCAGCTTCAATGGTCAACAGA (SEQ ID NO: 83) |
| Cytochrome P450 (2) | Reverse | CAACTAGGTTTAATGGGAAATGATAGG (SEQ ID NO: 84) |
| Arginine Kinase | Forward | GAAAGAAATGAATGACGGAATCG (SEQ ID NO: 85) |
| Arginine Kinase | Reverse | TTTGCCTTGTGTATAGCAATCGA (SEQ ID NO: 86) |
| Dopachrome | Forward | CCTGGAATGATGGCATATTCG (SEQ ID NO: 87) |
| Dopachrome | Reverse | TGAAACTCTCGGAAGCTGGATAA (SEQ ID NO: 88) |
| FPPS1 | Forward | CTGTTGAAAAAAAAATCGGTGAACT (SEQ ID NO: 89) |
| FPPS1 | Reverse | TCAACATTATGATTTCCGTCTCCAT (SEQ ID NO: 90) |
| Juvenile hormone | Forward | AGGAAAACCCAAAATGGCAAT (SEQ ID NO: 91) |
| Juvenile hormone | Reverse | ATGTATTCTTCTTTTGGATCTTTTCTTGAG (SEQ ID NO: 92) |
| 18S | Forward | ATGCCCCCGCCTGTCCTTATT (SEQ ID NO: 93) |
| 18S | Reverse | TGAAAGCAGCCTGAATAGTGG (SEQ ID NO: 94) |

Example 3

RNAi of Vitellogenin Gene Expression in a Concentration Dependent Manner

Vitellogenin is an important group of proteins synthesized extraovarially and is essential for development of the major egg yolk protein, vitellin. Synthesis and uptake of vitellin by developing oocytes are necessary in the reproductive process of insects (Tufail & Takeda, J. Insect Physiol., (2008) 54(12):1447-58). A previous report depleted vitellogenin expression using dsRNA microinjections in honeybees (*Apis mellifera*) resulted in reduced levels of vitellogenin and 96% of the treated animals exhibited a mutant phenotype (Amdam, G. V., BMC Biotech., (2003) 3:1). Vitellogenin was chosen as a target for gene silencing because a likely phenotypic effect is reduced fertility and fecundity which could facilitate biological control of BMSB. We tested the depletion of vitellogenin in BMSB in a concentration dependent manner. Green beans were immersed in dilutions of exogenous dsRNA consisting of 0.1, 1, 5, 10 and 20 µg was fed to the $4^{th}$ instar BMSB nymphs for 5 days. The resulting expression levels of Vg was monitored and the optimal depletion was compared for 1, 5 and 10 µg concentrations, which resulted in reduction of 1.6-, 2- and 1.4-fold, respectively, compared to the control (FIGS. 5A-5D). Hence 5 µg was considered as the optimal concentration of dsRNA for depletion of the vitellogenin gene in BMSB feeding assays.

Example 4

RNAi Mediated Depletion of Sesquiterpenes

The formation of juvenile hormone is in the later part of the mevalonate pathway by its precursor farnesyl diphosphate (FPP). FPP is sequentially transformed to farnesol, farnesoic acid, followed by methyl farneosate and finally to JH. This pathway is conserved in insects and arthropods specifically for metamorphosis, a process that is developmentally regulated by hormones (Bellé s et al, Ann. Rev. Entomol., (2005) 50:181-99; Nouzova et al, Insect Biochem. Mol. Biol., (2011) 41(9):660-69; Huang et al, PLoS One, (2015) 10(2):e0117291). Sesquiterpenoid compounds produced by such gene products as juvenile hormone and FPPS1 play central roles in insect reproduction, development, and behavior.

Sesquiterpenes are also involved in intra-species chemical communication in insects and these signal-carrying chemicals are known as pheromones. In BMSB, the male aggregation pheromone was recently examined and found to contain stereoisomers of the bisabolane skeleton and its epoxides (Khrimian et al., J. Nat. Prods., (2014) 77(7):1708-17. A study of JH biosynthesis in Bombyx mori showed a correlation between JH biosynthesis and expression of most JH biosynthetic enzymes in the corpora allata (CA) (Kinjoh et al, Insect Biochem. Mol. Biol., (2007) 37(8):808-18).

Figure 6A:
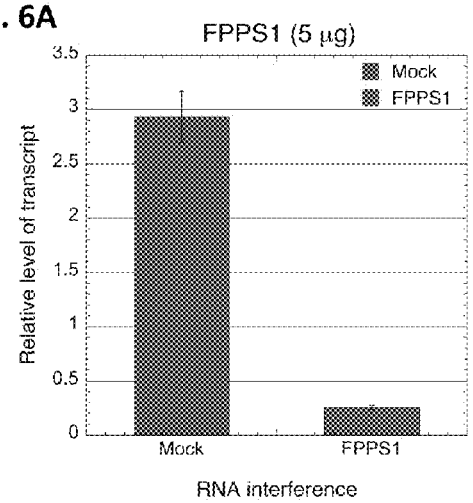
Figure 6B:
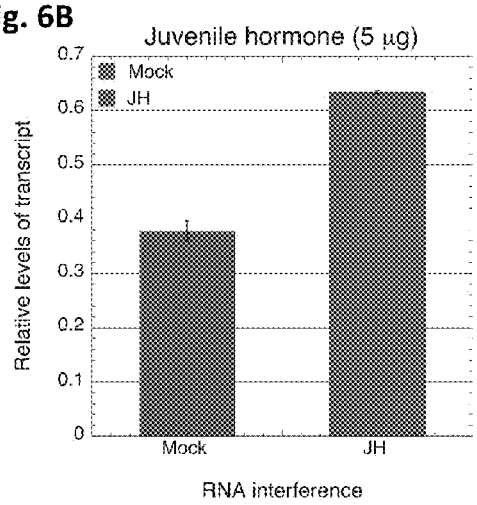
Figure 6C:
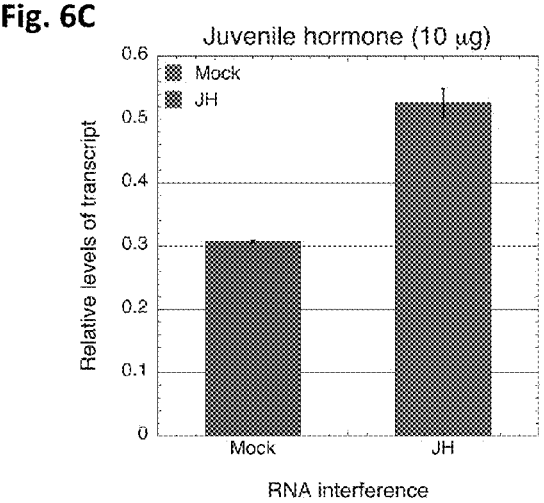
Figure 6D:
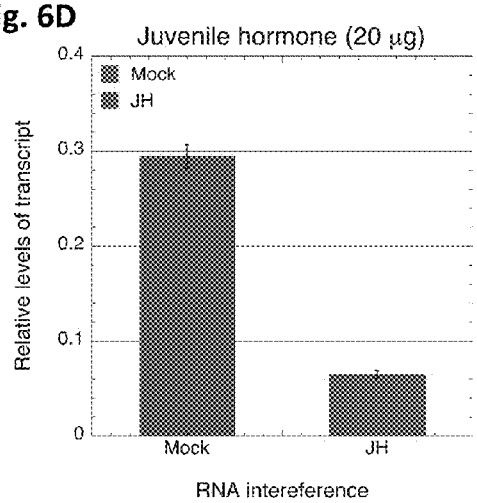

The specific BMSB genes for FPPS1 and JH of the sesquiterpenoid biosynthesis pathway were selected for depletion using RNAi. The dsRNA for FPPS1 and JH were in vitro transcribed to verify quality and stability (FIG. 2, lanes 15 and 16). Animals feeding on green beans immersed in 5 µg of FPPS1 dsRNA showed a dramatic decrease of approximately 12-fold (FIG. 6A). On the other hand, depletion of JH transcripts displayed hyperexpression of JH transcript when the animals were fed on green beans immersed in either 5 or 10 µg of dsRNA (FIGS. 6B and 6C). Although, when the concentration of dsRNA in the diet was increased to 20 µg, expression of the JH gene was diminished by 5-fold compared to the mock control (FIG. 6D). These results indicate a significant reduction in relative expression levels of FPPS1 and JH. It can also be inferred that using the vegetable-mediated delivery method, varying concentrations of dsRNA can be delivered in a dose dependent manner to fine-tune dosages leading to optimal RNAi.

In another separate study pheromone emission after feeding FPPS1 and LacZ dsRNA to newly molted adult males for 5 days was analyzed. RNAi-mediated knockdown of FPPS1 mRNA in BMSB males led to relatively reduced emission of (3S,6S,7R,10S)-10,11-epoxy-1-bisabolen-3-ol, a main component of a male-produced aggregation pheromone of BMSB.

Example 5

Combining dsRNA of FPPS1 and JH for Dual Gene Silencing Mutually Impedes Expression of the Other To test whether alterations in the expression of one sesquiterpenoid synthesis gene affected the other, $4^{th}$ instar nymphs were allowed to feed on either 5 or 20 µg of JH or FPPS1 dsRNA through the green bean delivery method for 5 days. Additionally, to test if silencing the two JH and FPPS1 genes had potential additive or synergistic effects, these dsRNAs were combined in the diet and the expression of both JH and FPPS1 transcripts were evaluated by qPCR. Observations revealed that animals fed on 5 µg dsRNA diet displayed a similar hyperexpression of JH transcripts in both JH or a combined diet of JH and FPPS1 (FIG. 7A). Intriguingly, RNAi against FPPS1 exhibited a 3-fold decrease in transcript levels (FIG. 7A). Though JH was not depleted, FPPS1 displayed a knockdown in gene expression. This may be due the threshold of RNAi where 5 µg of dsRNA was insufficient for hindering JH depletion but was enough to deplete FPPS1 in the JH biosynthesis pathway. When the concentration of dsRNA in the diet was increased to 20 µg, the level of JH gene expression was ablated by 47-fold in the JH dsRNA fed animals whilst a 2-fold drop was observed in the dual stacked RNAi animals (FIG. 7B).

Nymphs that fed on either a combination of JH and FPPS dsRNAs (at 5 µg each), or 5 µg of JH and FPPS1 individually, showed a significant 9- and 14- and 1.3-fold depletion of FPPS1 transcript respectively. This data showed that the depletion of FPPS1 transcript had a synergistic effect when the two dsRNAs were fed in combination (FIG. 7C). Interestingly, when 20 µg JH dsRNA diet was used either individually or in combination with 5 µg of FPPS1, the effect seems additive but the reduction in FPPS1 transcript in JH (20 µg) RNAi was reduced by 3-fold compared to the JH (5 µg) RNAi nymphs. Additionally, results also showed a lowered rate of molting in the FPPS1 treated animals.

Example 6

RNAi-mediated Depletion of JH Induced Lethality in BMSB

To investigate the long-term effects of RNAi in BMSB, five each of $4^{th}$ instar BMSB nymphs were allowed to feed on in vitro transcribed gene specific dsRNA for FPPS1, JH, Vg and by stacking FPPS1+JH and JH+Vg dsRNAs using the green bean diet. It was observed that control and mock treated nymphs were physically more developed when compared to dsRNA treated insects. The first nymphal-adult eclosion was observed from the mock treated insects after 10 days (FIG. 8A, panel a). However, insects treated with JH dsRNA alone, or with stacked FPPS1+JH dsRNAs, showed slowed development and increased melanization, leading to death after day 13 (FIG. 8A, compare panels a to b and c). The body mass of these nymphs at different stages post dsRNA treatment was also monitored. JH dsRNA-induced RNAi severely affected the development of insects as observed by a continual decrease in body mass (FIG. 8B). Though there was no significant decrease in average body mass, a trend of decrease in body mass was observed in insects treated by stacked FPPS1+JH dsRNA when compared to controls (FIG. 8B). All control-, mock-, FPPS- and Vg-dsRNA treated insects molted to adults, while only one or two reached adulthood when fed with stacked dsRNAs for FPPS1+JH and JH+Vg, respectively. None of the insects feeding on JH dsRNA enclosed to adults; instead all died between days 11 and 13. Two insects each fed on FPPS, Vg, FPPS1+JH or JH+Vg dsRNA died while only one died from mock, indicating RNAi mediated silencing of JH affected nymphal-adult development in BMSB ultimately leading to their mortality.

Example 7

RNAi Mediated Depletion of FPPS1 Affected Pheromone Emission in Adult BMSB

Sesquiterpenes are involved in intra species chemical communication in insects involving
biological events such as development and metamorphosis (Riddiford, L. M., Gen. Comp. Endocrinol., (2012) 179:447-84) such as the mevalonate pathway and JH biosynthesis in insects (Bellé s, et al., Ann. Rev. Entomol., (2005) 50:181-99). In BMSB the male aggregation pheromone was recently examined and found to contain stereoisomers of the bisabolane skeleton and its epoxides, 3S,6S,7R,10S)-10,11-epoxy-1-bisabolen-3-ol and (3R,6S,7R,10S)-10,11-epoxy-1-bisabolen-3-ol that attracted males, females and nymphs (Khrimian et al., J. Nat. Prod., (2014) 77:1708-17).

To test if the BMSB aggregation pheromone production was affected by FPPS1, RNAi was used to examine the role of FPPS1 in aggregation pheromone biosynthesis in vivo. To measure pheromone production, BMSB were placed in the chambers (1-quart wide mouth canning jar) fitted with a Teflon cover (Savillex®) equipped with two tubes, one an air inlet to reach into the bottom of the jar, and the second a glass tube (180 mm×4 mm I.D.) containing activated charcoal (0.21 g, Aldrich; Darco 20-40 mesh). House air (2-3 psig) was purified through a charcoal trap (Aldrich; Darco 20-40 mesh), then humidified before feeding a manifold from which it was fed to the chambers. The actual airflow through each chamber was regulated to 1 L/min via its flow meter (K Instruments model FR2A14BVBN). The air containing BMBS volatiles was withdrawn from the chambers through charcoal traps via a house vacuum. A pressure relief/vacuum breaker valve was installed at the inlet of the supply manifold to maintain a plus or minus two inches of water over or under ambient pressure. At specified collection times, trapped volatiles were extracted from the charcoal with hexanes to collect 1 mL solutions. The samples were then transferred to an Agilent auto sampler injector 7683 Series and analyzed using an Agilent GC/Mass spectrometer (7890A\5995C) on an Agilent HP-5 column (30 m×250 μm×0.25 μm). Helium was used as a carrier gas at 1 ml/min. Samples were injected splitless at 260° C. Oven program: 40° C. (5) to 270° C. (3) at 10° C.

Figure 9:
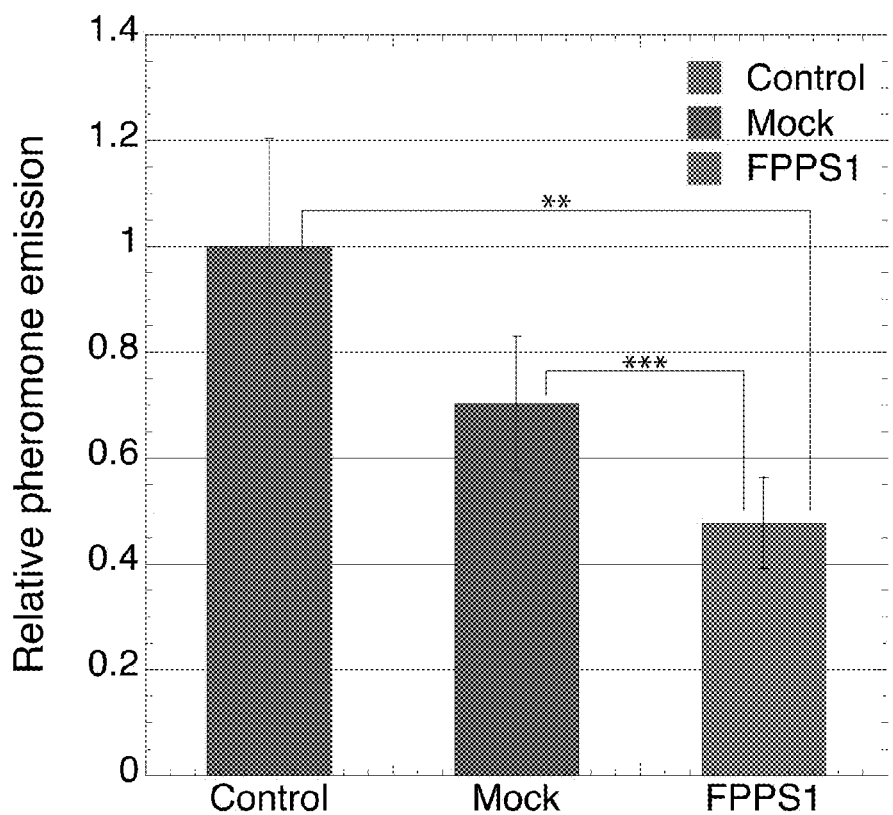
FIG. 9 provides graphic representation of the effect of RNAi on aggregation pheromone production in BMSB.

Males fed on green bean diet containing 5 μg of FPPS1 dsRNA showed significant 1.4- and 2-fold reduced levels of emitted pheromone compared with mock treated and untreated adults respectively (FIG. 9).

While the invention has been described with reference to details of the illustrated embodiments, these details are not intended to limit the scope of the invention as defined in the appended claims. The embodiment of the invention in which exclusive property or privilege is claimed is defined as follows:

---

What is claimed is:

1. A double-stranded ribonucleic acid (dsRNA) comprising a sense region with at least 95% sequence identity to any one of SEQ ID NOs: 56, 66, 67, or 68 and an antisense region comprising a second sequence complementary to the sense region, wherein said dsRNA is capable of inducing ribonucleic acid interference (RNAi) in an insect.

2. The dsRNA of claim 1, wherein the sense region has at least 99% or 100% sequence identity to any one of SEQ ID NOs: 56, 66, 67, or 68.

3. The dsRNA of claim 1, wherein the dsRNA is distributed throughout at least part of a living plant material's vascular tissues.

4. The dsRNA of claim 3, wherein the living plant material is a fruit, vegetable, stem or leaf.

5. The dsRNA of claim 1, wherein the dsRNA is expressed in a bacterial or yeast cell.

6. The dsRNA of claim 1, wherein the dsRNA is expressed in a transgenic plant cell.

7. The dsRNA of claim 1, wherein the insect is a brown marmorated stink bug.

8. A method of controlling *H. halys* comprising applying one or more dsRNA molecules of claim 1 to a living plant material such that the one or more dsRNA molecules are taken up and distributed by the vascular tissue of the living plant material and allowing the one or more insects to ingest an effective amount of the one or more dsRNA molecules to induce RNAi, thereby controlling the one or more insects.

9. The method of claim 8, wherein the one or more dsRNA molecules comprise a first dsRNA molecule and a second dsRNA molecule, wherein the first dsRNA molecule comprises a sense region with at least 95% sequence identity to SEQ ID NO: 56 and an antisense region comprising a second sequence complementary to the sense region and wherein the second dsRNA molecule comprises a sense region with at least 95% sequence identity to SEQ ID NO: 68 and an antisense region comprising a second sequence complementary to the sense region.

10. A method of controlling *H. halys* comprising the steps of:
   a) providing a living plant material containing at least one double-strand RNA (dsRNA) wherein the at least one dsRNA molecule comprises a sense region with at least 95% sequence identity to SEQ ID NOs: 56, 66, 67, or 68 and an antisense region comprising a second sequence complementary to the sense region, wherein the at least one dsRNA molecule is distributed throughout at least part of the living plant material's vascular tissues and wherein the living plant material does not contain genetic information allowing for the production of the at least one double strand dsRNA molecule;
   b) allowing the insect to ingest a sufficient amount of the at least one dsRNA molecule, by feeding on the plant material, to interfere with the production of at least one protein targeted by the at least one dsRNA molecule, thereby inducing RNAi in the insect, and;
   c) controlling the insect via RNAi.

11. The method of claim 10, wherein the living plant material is a fruit, vegetable, stem or leaf.

12. The method of claim 11, wherein the living plant material is a green bean.

13. The method of claim 10, wherein the at least one dsRNA molecule comprises two dsRNA molecules wherein the first dsRNA molecule comprises a sense region with at least 95% sequence identity to SEQ ID NO: 56 and an antisense region comprising a second sequence complementary to the sense region and wherein the second dsRNA molecule comprises a sense region with at least 95% sequence identity to SEQ ID NO: 68 and an antisense region comprising a second sequence complementary to the sense region.

* * * * *